(12) United States Patent
Kaushikkar et al.

(10) Patent No.: US 7,991,560 B2
(45) Date of Patent: Aug. 2, 2011

(54) SYSTEM, METHOD, AND COMPUTER SOFTWARE FOR THE PRESENTATION AND STORAGE OF ANALYSIS RESULTS

(75) Inventors: Shantanu V. Kaushikkar, San Jose, CA (US); Teresa Webster, Loma Mar, CA (US); Rui Mei, Santa Clara, CA (US); Linda McAllister, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1131 days.

(21) Appl. No.: 11/352,008

(22) Filed: Feb. 10, 2006

(65) Prior Publication Data
US 2006/0167636 A1 Jul. 27, 2006

Related U.S. Application Data

(62) Division of application No. 10/219,882, filed on Aug. 15, 2002, now Pat. No. 7,031,846.

(60) Provisional application No. 60/312,906, filed on Aug. 16, 2001.

(51) Int. Cl.
*G06F 7/00* (2006.01)

(52) U.S. Cl. .............. 702/19; 702/20; 703/11; 707/700; 435/6; 536/24.5

(58) Field of Classification Search ........................ None
See application file for complete search history.

(56) References Cited

U.S. PATENT DOCUMENTS

| | | | |
|---|---|---|---|
| 6,300,078 B1 | 10/2001 | Friend et al. | |
| 6,408,308 B1 * | 6/2002 | Maslyn et al. | 707/776 |
| 6,453,241 B1 | 9/2002 | Bassett, Jr. et al. | |
| 2002/0016680 A1 | 2/2002 | Wang et al. | |
| 2002/0029113 A1 | 3/2002 | Wang et al. | |
| 2002/0059326 A1 | 5/2002 | Bernhart et al. | |
| 2002/0103604 A1 | 8/2002 | Liu et al. | |
| 2002/0165674 A1 | 11/2002 | Bassett, Jr. et al. | |
| 2003/0009292 A1 | 1/2003 | Mei et al. | |
| 2003/0096243 A1 * | 5/2003 | Busa | 435/6 |
| 2004/0138821 A1 | 7/2004 | Chiles et al. | |

FOREIGN PATENT DOCUMENTS

| | | |
|---|---|---|
| WO | WO 01/21839 A2 | 3/2001 |
| WO | WO 02/095659 A2 | 11/2002 |

OTHER PUBLICATIONS

Fan et al. 2000 Genome Research, vol. 10 pp. 853-860.*
Fan, J-B et al. Parallel Genotypingof Human SNP's Using Generic High-Density Oligonucleotide Tag Arrays. Genome Research, Jun. 2000, vol. 10, pp. 853-860.

* cited by examiner

*Primary Examiner* — Mary Zeman
(74) *Attorney, Agent, or Firm* — Steven M. Yee; Thomas J. Siepmann

(57) ABSTRACT

A computer program product, and related systems and methods, are described that processes emission intensity data corresponding to probes of a biological probe array. The computer program includes a genotype and statistical analysis manager that determines absolute or relative expression values based, at least in part, on a statistical measure of the emission intensity data and at least one user-selectable statistical parameter. The analysis manager may also determine genotype calls for one or more probes based, at least in part, on the emission intensity data. The analysis manager may further display the absolute or relative expression values based, at least in part, on at least one user-selectable display parameter and/or a measure of normalized change between genotype calls. The measure of normalized change may be based, at least in part, on a comparison of genotype calls and a reference value.

20 Claims, 7 Drawing Sheets

FIG. 5B

Report Type: Genotyping Analysis Viewer Report
Date:

CEL Filenames (1st Pair): 1204-S24A.CEL, 1204-S24B.CEL
CEL Filenames (2nd Pair): 1204-S23A.CEL, 1204-S23B.CEL
Probe Array Type: HuSNP
Algorithm: Genotyping
Alg Version: 4.0
Alg Parameters: NumStdCutoff=1.50 SCutoff=1.30 MinMBNum=3

GRAPHICAL USER INTERFACE 382B

QUALITATIVE GENOTYPE CALL 530

512 RELATIVE ALLELE SIGNAL DIFFERENCE

| Marker | Chromosome | EstGenDist | 1204-S24 Call | RAS1 | RAS2 | 1204-S23 Call | RAS1 | RAS2 | 1204-S24_1204-S23 Delta RAS |
|---|---|---|---|---|---|---|---|---|---|
| WIAF-2729 | 10 | | AB | 0.672 | -1000 | A | 0.971 | -1000 | 0.299 |
| WIAF-2460 | | | AB | 0.721 | -1000 | A | 0.994 | -1000 | 0.272 |
| WIAF-2184 | 19 | 44.10 | AB | 0.466 | -1000 | B | 0.000 | -1000 | 0.466 |
| WIAF-3272 | 1 | | AB | 0.428 | -1000 | A | 0.945 | -1000 | 0.516 |

FIG. 6

GRAPHICAL USER INTERFACE 382C

| | Analysis Name | Probe Set Name | Stat Pairs | Stat Pairs Used | Signal | Detection | Detection p-value |
|---|---|---|---|---|---|---|---|
| | | PROBE SET IDENTIFIER 520 | | EMISSION INTENSITY DATA 625 | | DETECTION CALL 620 | P-VALUE 630 |
| 1 | Hu6800 | AFFX-BioB-5_at | 20 | 20 | 91.1 | A | 0.175328 |
| 2 | Hu6800 | AFFX-BioB-M_at | 20 | 20 | 77.0 | A | 0.062929 |
| 3 | Hu6800 | AFFX-BioB-3_at | 20 | 20 | 170.7 | P | 0.021902 |
| 4 | Hu6800 | AFFX-BioC-5_at | 20 | 20 | 357.8 | P | 0.002556 |
| 5 | Hu6800 | AFFX-BioC-3_at | 20 | 20 | 253.1 | P | 0.001796 |
| 6 | Hu6800 | AFFX-BioDn-5_at | 20 | 20 | 293.7 | P | 0.002275 |
| 7 | Hu6800 | AFFX-BioDn-3_at | 20 | 20 | 2456.2 | P | 0.000754 |
| 8 | Hu6800 | AFFX-CreX-5_at | 20 | 20 | 3243.4 | P | 0.000044 |
| 9 | Hu6800 | AFFX-CreX-3_at | 20 | 20 | 5361.6 | P | 0.000044 |
| 10 | Hu6800 | AFFX-BioB-5_st | 20 | 20 | 11.3 | A | 0.659339 |
| 11 | Hu6800 | AFFX-BioB-M_st | 20 | 20 | 18.9 | A | 0.927300 |
| 12 | Hu6800 | AFFX-BioB-3_st | 20 | 20 | 12.6 | A | 0.973889 |
| 13 | Hu6800 | AFFX-BioC-5_st | 20 | 20 | 22.0 | A | 0.794268 |
| 14 | Hu6800 | AFFX-BioC-3_st | 20 | 20 | 19.8 | A | 0.686277 |
| 15 | Hu6800 | AFFX-BioDn-5_st | 20 | 20 | 82.2 | A | 0.275146 |
| 16 | Hu6800 | AFFX-BioDn-3_st | 20 | 20 | 59.6 | A | 0.500000 |
| 17 | Hu6800 | AFFX-CreX-5_st | 20 | 20 | 39.9 | A | 0.396920 |
| 18 | Hu6800 | AFFX-CreX-3_st | 20 | 20 | 21.7 | A | 0.485110 |
| 19 | Hu6800 | hum_alu_at | 69 | 64 | 18528.3 | P | 0.000000 |
| 20 | Hu6800 | AFFX-DapX-5_at | 20 | 20 | 49.8 | M | 0.046482 |

SYSTEM, METHOD, AND COMPUTER SOFTWARE FOR THE PRESENTATION AND STORAGE OF ANALYSIS RESULTS

RELATED APPLICATIONS

The present application is a divisional application of and claims priority to U.S. application Ser. No. 10/219,882, titled "Method, System, and Computer Software for the Presentation and Storage of Analysis Results", filed Aug. 15, 2002, which claims priority to U.S. Provisional Patent Application No. 60/312,906, titled "METHODS AND SYSTEMS FOR EVALUATING ALLELIC IMBALANCE AND PERFORMING OTHER GENOMIC ANALYSIS FUNCTIONS" filed Aug. 16, 2001, each of which is hereby incorporated by reference herein in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

1. Field of the Invention

The present invention relates to the field of bioinformatics. In particular, the present invention relates to computer systems, methods, and products for the storage and presentation of data resulting from the analysis of microarrays of biological materials.

2. Related Art

Research in molecular biology, biochemistry, and many related health fields increasingly requires organization and analysis of complex data generated by new experimental techniques. The rapidly evolving field of bioinformatics addresses these tasks. See, e.g., H. Rashidi and K. Buehler, *Bioinformatics Basics: Applications in Biological Science and Medicine* (CRC Press, London, 2000); *Bioinformatics: A Practical Guide to the Analysis of Gene and Proteins* (B. F. Ouelette and A. D. Bzevanis, eds., Wiley & Sons, Inc.; 2d ed., 2001), both of which are hereby incorporated herein by reference in their entireties. Broadly, one area of bioinformatics applies computational techniques to large genomic databases, often distributed over and accessed through networks such as the Internet, for the purpose of illuminating relationships among gene structure and/or location, protein function, and metabolic processes.

The expanding use of microarray technology is one of the forces driving the development of bioinformatics. Spotted arrays, such as those made using the Affymetrix® 417™ or 427™ Arrayer from Affymetrix, Inc. of Santa Clara, Calif., are used to generate information about biological systems. Also, synthesized probe arrays, such as Affymetrix® GeneChip® arrays, have been widely used to generate unprecedented amounts of information about biological systems. For example, the GeneChip® Human Genome U133 Set (HG-U133A and HG-U133B) is made up of two microarrays containing over 1,000,000 unique oligonucleotide features covering more than 39,000 transcript variants that represent more than 33,000 human genes. Experimenters can quickly design follow-on experiments with respect to genes, EST's, or other biological materials of interest by, for example, producing in their own laboratories microscope slides containing dense arrays of probes using the Affymetrix® 417™ or 427™ Arrayer, or other spotting device.

Analysis of data from experiments with synthesized and/or spotted probe arrays may lead to the development of new drugs and new diagnostic tools. In some applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner.

There is a great demand in the art for methods for organizing, accessing and analyzing the vast amount of information collected by scanning microarrays. Computer-based systems and methods have been developed to assist a user to obtain, analyze, and visualize the vast amounts of information generated by the scanners. These commercial and academic software applications typically provide such information as intensities of hybridization reactions or comparisons of hybridization reactions. This information may be displayed to a user in graphical form. In particular, data representing detected emissions conventionally are stored in a memory device of a computer for processing. The processed images may be presented to a user on a video monitor or other device, and/or operated upon by various data processing products or systems.

In particular, microarrays and associated instrumentation and computer systems have been developed for rapid and large-scale collection of data about the expression of genes or expressed sequence tags (EST's) in tissue samples. The data may be used, among other things, to study genetic characteristics and to detect mutations relevant to genetic and other diseases or conditions. More specifically, the data gained through microarray experiments is valuable to researchers because, among other reasons, many disease states can potentially be characterized by differences in the expression levels of various genes, either through changes in the copy number of the genetic DNA or through changes in levels of transcription (e.g., through control of initiation, provision of RNA precursors, or RNA processing) of particular genes. Thus, for example, researchers use microarrays to answer questions such as: Which genes are expressed in cells of a malignant tumor but not expressed in either healthy tissue or tissue treated according to a particular regime? Which genes or EST's are expressed in particular organs but not in others? Which genes or EST's are expressed in particular species but not in others? How does the environment, drugs, or other factors influence gene expression? Data collection is only an initial step, however, in answering these and other questions. Researchers are increasingly challenged to extract biologically meaningful information from the vast amounts of data generated by microarray technologies, and to design follow-on experiments. A need exists to provide researchers with improved tools and information to perform these tasks.

SUMMARY OF THE INVENTION

Systems, methods, and computer program products are described herein to address these and other needs. In accordance with one embodiment, a method is described that includes receiving first emission intensity data and second emission intensity data corresponding to probes of a probe array; determining first and second genotype calls for one or more probe sets, each having one or more probes, based, at least in part, on the first and second emission intensity data; comparing a first of the first genotype calls with a corresponding first of the second genotype calls and with a reference value; and displaying a measure of normalized change between the first and second genotype calls based, at least in part, on the comparison of first and second genotype calls and reference value. The emission intensity data may include a statistical measure of pixel values corresponding to the probes. The probe array may include a synthesized probe array or a spotted probe array. The genotype call may include a biallelic call, which may include combinations of two alleles. Also, the biallelic call may include a relative allele signal that includes a numerical value between a range, wherein calls near one extreme of the range correspond to one type of homozygous call, calls near the opposing extreme of the range correspond to a second type of homozygous call, and intermediate calls in an intermediate sub-range within the range correspond to a heterozygous call. The reference value may include a standard deviation value.

In this and other embodiments, the step of displaying a measure of normalized change may include displaying a graphical user interface, which may display information in text and/or graphical formats. In some implementations, the graphical user interface includes one or more associations of identification data with the measure of normalized change. The identification data may include probe set identifiers, one or more SNP locations, one or more genotype calls, one or more relative allele signals, or any combination thereof. The one or more SNP locations may include chromosome number and/or estimated genetic distance. For example, the estimated genetic distance may be a relative measure of a distance from a SNP location to the top of the short arm of a chromosome, such as may be expressed in centimorgans. The identification data may be displayed in a geometric association with the measure of normalized change, such as by columns or rows of graphical or textual elements. The identification data may also, or in the alternative, be displayed in a color, shade, or intensity association with the measure of normalized change.

In accordance with a further embodiment, a method is described that includes receiving first emission intensity data and second emission intensity data corresponding to probes of a probe array, wherein the first and second emission intensity data include a statistical measure of pixel values corresponding to the probes; determining first and second genotype calls for one or more probe sets, each having one or more probes based, at least in part, on the first and second emission intensity data; comparing a first of the first genotype calls with a corresponding first of the second genotype calls; and displaying a measure of normalized change between the first and second genotype calls. The measure of normalized change may be based, at least in part, on the comparison of first and second genotype calls and reference value.

A computer program product is described in accordance with another embodiment. The product includes an input manager that receives first emission intensity data and second emission intensity data corresponding to probes of a probe array; a genotype analysis determiner that determines first and second genotype calls for one or more probe sets, each having one or more probes based, at least in part, on the first and second emission intensity data; a genotype comparator that compares a first of the first genotype calls with a corresponding first of the second genotype calls and with a reference value; and an output manager that displays a measure of normalized change between the first and second genotype calls. The measure of normalized change may be based, at least in part, on the comparison of first and second genotype calls and reference value.

In accordance with yet another embodiment, a method is described that includes receiving one or more sets of emission intensity data corresponding to probes of a biological probe array; determining absolute or relative expression values based, at least in part, on a statistical measure of the emission intensity data and at least one user-selectable statistical parameter; and displaying the absolute or relative expression values based, at least in part, on at least one user-selectable display parameter.

A computer program product is described in accordance with a further embodiment. The product includes an input manager that receives one or more sets of emission intensity data corresponding to probes of a biological probe array; a statistical analysis determiner that determines absolute or relative expression values based, at least in part, on a statistical measure of the emission intensity data and at least one user-selectable statistical parameter; and an output manager that displays the absolute or relative expression values based, at least in part, on at least one user-selectable display parameter. In accordance with yet a further embodiment, a computer program product, includes an input manager that receives one or more sets of emission intensity data corresponding to probes of a biological probe array, and a genotype and statistical analysis manager. The manager determines absolute or relative expression values based, at least in part, on a statistical measure of the emission intensity data and at least one user-selectable statistical parameter, and is further constructed and arranged, when the one or more sets of emission intensity data include first and second sets of emission intensity data, to determine first and second genotype calls for one or more probe sets, each having one or more probes based, at least in part, on the first and second sets of emission intensity data, and is yet further constructed and arranged to display the absolute or relative expression values based, at least in part, on at least one user-selectable display parameter and a measure of normalized change between the first and second genotype calls based, at least in part, on the comparison of first and second genotype calls and reference value.

In accordance with another embodiment, a system is described that includes a scanner constructed and arranged to provide emission intensity data corresponding to probes of a biological probe array. The system also has a computer constructed and arranged to execute a computer program product including an input manager that receives one or more sets of the emission intensity data. The computer program product also has a genotype and statistical analysis manager constructed and arranged to determine absolute or relative expression values based, at least in part, on a statistical measure of the emission intensity data and at least one user-selectable statistical parameter. The manager is further constructed and arranged, when the one or more sets of emission intensity data include first and second sets of emission intensity data, to determine first and second genotype calls for one or more probe sets, each having one or more probes based, at least in part, on the first and second sets of emission intensity data. The manager is yet further constructed and arranged to display the absolute or relative expression values based, at least in part, on at least one user-selectable display parameter and a measure of normalized change between the first and second genotype calls based, at least in part, on the comparison of first and second genotype calls and reference value.

The above implementations are not necessarily inclusive or exclusive of each other and may be combined in any manner that is non-conflicting and otherwise possible, whether they be presented in association with a same, or a different, aspect or implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF THE DRAWINGS

In the drawings, like reference numerals indicate like structures or method steps and the leftmost digit of a reference numeral indicates the number of the figure in which the referenced element first appears (for example, the element 120 appears first in FIG. 1). In functional block diagrams, rectangles generally indicate functional elements, parallelograms generally indicate data, and rectangles with a pair of double borders generally indicate predefined functional elements. These conventions, however, are intended to be typical or illustrative, rather than limiting.

FIGS. 5A and 5B are graphical illustration of particular implementations of the report data file of FIG. 4; and FIG. 6 is a graphical illustration of a particular implementation of the analysis output data file of FIG. 4.

DETAILED DESCRIPTION

Systems, methods, and computer products are now described with reference to an illustrative embodiment referred to as genotype and statistical analysis manager 400. Manager 400 is shown in a computer system environment in FIG. 4 with examples of graphical user interface output presented in FIGS. 5A, 5B and 6. In a typical implementation, manager 400 may be used to provide a user with information related to results from experiments with probe arrays. More specifically, manager 400 determines absolute or relative expression values based, at least in part, on a statistical measure of the emission intensity data and at least one user-selectable statistical parameter. Also, when the one or more sets of emission intensity data include first and second sets of emission intensity data, manager 400 determines first and second genotype calls for one or more probe sets, each having one or more probes based, at least in part, on the first and second sets of emission intensity data. Further, manager 400 may display the absolute or relative expression values based, at least in part, on at least one user-selectable display parameter and a measure of normalized change between the first and second genotype calls based, at least in part, on the comparison of first and second genotype calls and a reference value. The experiments often involve the use of scanning equipment to detect hybridization of probe-target pairs, and the analysis of detected hybridization by various software applications. Illustrative systems and software applications suitable for implementation of the present invention are now described in relation to FIGS. 1 through 3.

Figure 1:
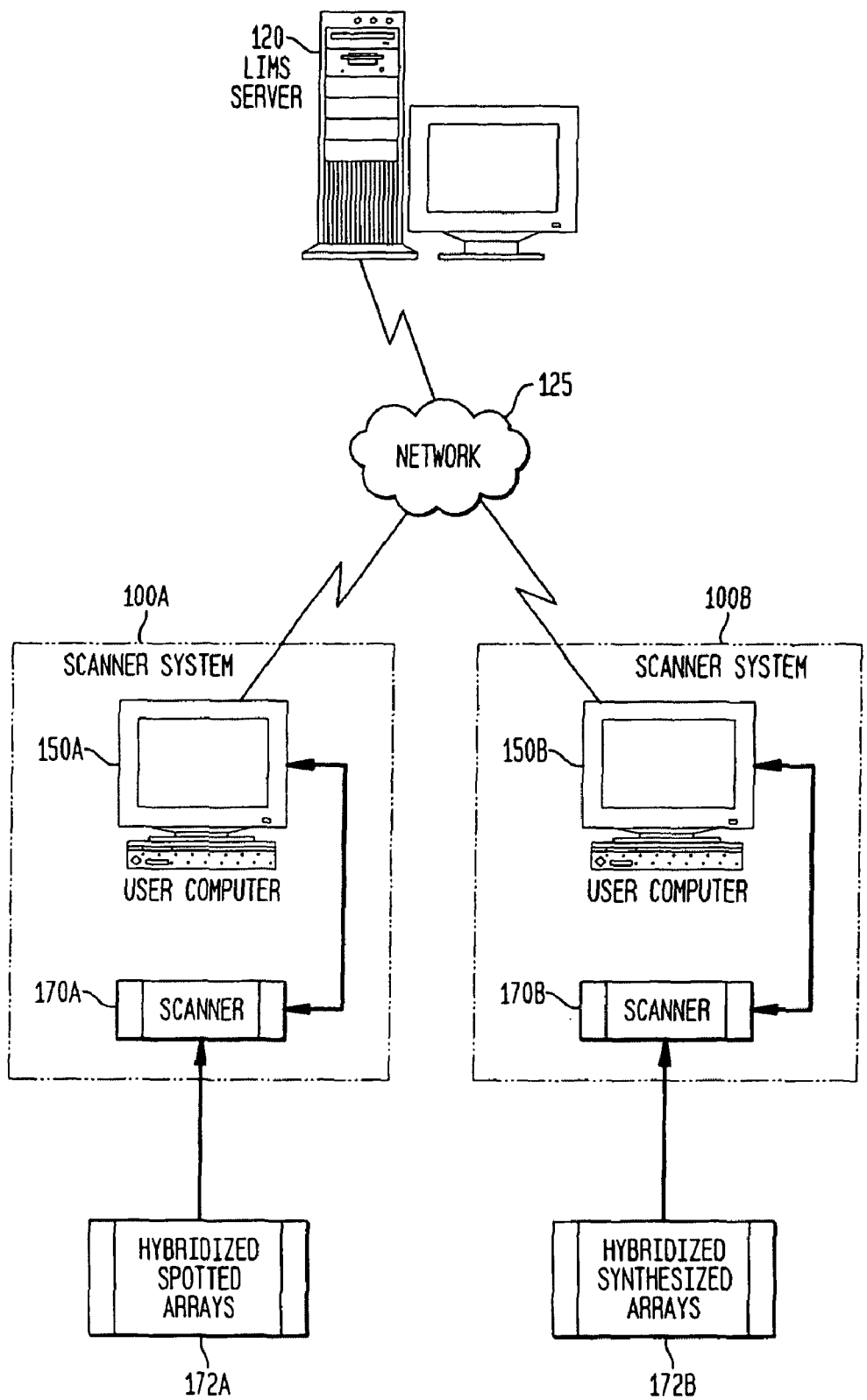
FIG. 1 is a functional block diagram of one implementation of a laboratory information management system that is connected to a plurality of user computers via a network.

FIG. 1 is a simplified schematic diagram of illustrative systems for generating, sharing, and processing data derived from experiments using probe arrays, such as illustrative hybridized spotted arrays 172A and hybridized synthesized arrays 172B (generally and collectively referred to as probe arrays 172). In this example, illustrative scanner systems 100A and 100B (generally and collectively referred to as scanner system 100) are used to scan probe arrays 172. A scanner system 100 typically may include a user computer (e.g., user computers 150A and 150B, generally and collectively referred to as user computer 150) and a scanner (e.g., scanners 170A and 170B, generally and collectively referred to as scanner 170). In this example, data may be communicated between user computer 150 and Laboratory Information Management (LIMS) server 120 over network 125. LIMS server 120 and associated software generally provides data capturing, tracking, and analysis functions from a centralized infrastructure. Aspects of illustrative LIMS are described in U.S. patent applications Ser. Nos. 09/683,912 and 09/682,098; and in U.S. Provisional Patent Applications Nos. 60/220,587 and 60/273,231, all of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 150A and 150B, a single computer may be used in other implementations. Further, user computer 150, or any functional components thereof, may also or in addition be integral to scanner 170 in some implementations so that, for example, it is located within the same housing as the scanner.

More generally, a large variety of computer and/or network architectures and designs may be employed, and it will be understood by those of ordinary skill in the relevant art that many components of typical computer network systems are not shown in FIG. 1. Components of illustrative computers are described in greater detail below in relation to FIGS. 2 and 3.

Probe Arrays 172: Various techniques and technologies may be used for synthesizing dense arrays of biological materials on or in a substrate or support. For example, Affymetrix® GeneChip® arrays are synthesized in accordance with techniques sometimes referred to as VLSIPS™ (Very Large Scale Immobilized Polymer Synthesis) technologies. Some aspects of VLSIPS™ and other microarray manufacturing technologies are described in U.S. Pat. Nos. 5,424,186; 5,143,854; 5,445,934; 5,744,305; 5,831,070; 5,837,832; 6,022,963; 6,083,697; 6,291,183; 6,309,831; and 6,310,189, all of which are hereby incorporated by reference in their entireties for all purposes. The probes of these arrays in some implementations consist of nucleic acids that are synthesized by methods including the steps of activating regions of a substrate and then contacting the substrate with a selected monomer solution. As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. Nucleic acids may include any deoxyribonucleotide, ribonucleotide, and/or peptide nucleic acid component, and/or any chemical variants thereof such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Probes of other biological materials, such as peptides or polysaccharides as non-limiting examples, may also be formed. For more details regarding possible implementations, see U.S. Pat. No. 6,156,501, which is hereby incorporated by reference herein in its entirety for all purposes.

A system and method for efficiently synthesizing probe arrays using masks is described in U.S. patent application Ser. No. 09/824,931; a system and method for a rapid and flexible microarray manufacturing and online ordering system is described in U.S. Provisional Patent Application Ser. No. 60/265,103; and systems and methods for optical photolithography without masks are described in U.S. Pat. No. 6,271,957 and in U.S. patent application Ser. No. 09/683,374, all of which are hereby incorporated by reference herein in their entireties for all purposes.

The probes of synthesized probe arrays typically are used in conjunction with biological target molecules of interest, such as cells, proteins, genes or EST's, other DNA sequences, or other biological elements. More specifically, the biological molecule of interest may be a ligand, receptor, peptide, nucleic acid (oligonucleotide or polynucleotide of RNA or DNA), or any other of the biological molecules listed in U.S. Pat. No. 5,445,934 (incorporated by reference above) at column 5, line 66 to column 7, line 51. For example, if transcripts of genes are the interest of an experiment, the target molecules would be the transcripts. Other examples include protein fragments, small molecules, etc. Target nucleic acid refers to a nucleic acid (often derived from a biological sample) of interest. Frequently, a target molecule is detected using one or more probes. As used herein, a probe is a molecule for detecting a target molecule. A probe may be any of the molecules in the same classes as the target referred to above. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation. As noted above, a probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

The samples or target molecules of interest (hereafter, simply targets) are processed so that, typically, they are spatially associated with certain probes in the probe array. For example, one or more tagged targets are distributed over the probe array. In accordance with some implementations, some targets hybridize with probes and remain at the probe locations, while non-hybridized targets are washed away. These hybridized targets, with their tags or labels, are thus spatially associated with the probes. The hybridized probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. Nos. 5,800,992 and 6,040,138, and International Application No. PCT/US98/15151, published as WO99/05323), genotyping (U.S. Pat. No. 5,856,092), or other detection of nucleic acids, all of which are hereby incorporated by reference herein in their entireties for all purposes.

Other techniques exist for depositing probes on a substrate or support. For example, "spotted arrays" are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. The Affymetrix® 417™ Arrayer and 427™ Arrayer are devices that deposit densely packed arrays of biological materials on microscope slides in accordance with these techniques. Aspects of these, and other, spot arrayers are described in U.S. Pat. Nos. 6,040,193 and 6,136,269; in U.S. patent application Ser. No. 09/683,298, in U.S. Provisional Patent Application No. 60/288,403; and in PCT Application No. PCT/US99/00730 (International Publication Number WO 99/36760), all of which are hereby incorporated by reference in their entireties for all purposes. Other techniques for generating spotted arrays also exist. For example, U.S. Pat. No. 6,040,193 to Winkler, et al. is directed to processes for dispensing drops to generate spotted arrays. The '193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Other implementations of the jetting technique may use devices such as syringes or piezo electric pumps to propel the biological material. It will be understood that the foregoing are non-limiting examples of techniques for synthesizing, depositing, or positioning biological material onto or within a substrate. For example, although a planar array surface is preferred in some implementations of the foregoing, a probe array may be fabricated on a surface of virtually any shape or even a multiplicity of surfaces. Arrays may comprise probes synthesized or deposited on beads, fibers such as fiber optics, glass or any other appropriate substrate, see U.S. Pat. Nos. 6,361,947, 5,770,358, 5,789,162, 5,708,153 and 5,800,992, all of which are hereby incorporated in their entireties for all purposes. Arrays may be packaged in such a manner as to allow for diagnostics or other manipulation of in an all inclusive device, see for example, U.S. Pat. Nos. 5,856,174 and 5,922,591 incorporated in their entireties by reference for all purposes.

To ensure proper interpretation of the term "probe" as used herein, it is noted that contradictory conventions exist in the relevant literature. The word "probe" is used in some contexts to refer not to the biological material that is synthesized on a substrate or deposited on a slide, as described above, but to what has been referred to herein as the "target." To avoid confusion, the term "probe" is used herein to refer to probes such as those synthesized according to the VLSIPS™ technology; the biological materials deposited so as to create spotted arrays; and materials synthesized, deposited, or positioned to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media.

Probes typically are able to detect the expression of corresponding genes or EST's by detecting the presence or abundance of mRNA transcripts present in the target. This detection may, in turn, be accomplished in some implementations by detecting labeled cRNA that is derived from cDNA derived from the mRNA in the target. In general, a group of probes, sometimes referred to as a probe set, contains subsequences in unique regions of the transcripts and does not correspond to a full gene sequence. Further details regarding the design and use of probes and probe sets are provided in U.S. Pat. No. 6,188,783; in PCT Application Serial No. PCT/US 01/02316, filed Jan. 24, 2001; and in U.S. patent application Ser. Nos. 09/721,042, 09/718,295, 09/745,965, and 09/764,324, all of which are hereby incorporated herein by reference in their entireties for all purposes.

Probe Set Identifiers: Probe-set identifiers typically come to the attention of a user, represented by user 275 of FIGS. 2 and 3, as a result of experiments conducted on probe arrays. For example, user 275 may select probe-set identifiers that identify microarray probe sets capable of enabling detection of the expression of mRNA transcripts from corresponding genes or EST's of particular interest. As is well known in the relevant art, an EST is a fragment of a gene sequence that may not be fully characterized, whereas a gene sequence generally is complete and fully characterized. The word "gene" is used generally herein to refer both to full size genes of known sequence and to computationally predicted genes. In some implementations, the specific sequences detected by the arrays that represent these genes or EST's may be referred to as, "sequence information fragments (SIF's)" and may be recorded in what may be referred to as a "SIF file." In particular implementations, a SIF is a portion of a consensus sequence that has been deemed to best represent the mRNA transcript from a given gene or EST. The consensus sequence may have been derived by comparing and clustering EST's, and possibly also by comparing the EST's to genomic sequence information. A SIF is a portion of the consensus sequence for which probes on the array are specifically designed. With respect to the operations of genotype and statistical analysis manager 400 of the particular implementation described herein, it is assumed with respect to some aspects that some microarray probe sets may be designed to detect the expression of genes based upon sequences of EST's.

As was described above, the term "probe set" refers in some implementations to one or more probes from an array of probes on a microarray. For example, in an Affymetrix® GeneChip® probe array, in which probes are synthesized on a substrate, a probe set may consist of 30 or 40 probes, half of which typically are controls. These probes collectively, or in various combinations of some or all of them, are deemed to be indicative of the expression of a gene or EST. In a spotted probe array, one or more spots may similarly constitute a "probe set."

The term "probe-set identifiers" is used broadly herein in that a number of types of such identifiers are possible and may be included within the meaning of this term in various implementations. One type of probe-set identifier is a name, number, or other symbol that is assigned for the purpose of identifying a probe set. This name, number, or symbol may be arbitrarily assigned to the probe set by, for example, the manufacturer of the probe array. A user may select this type of probe-set identifier by, for example, highlighting or typing the name. Another type of probe-set identifier as intended herein is a graphical representation of a probe set. For example, dots may be displayed on a scatter plot or other diagram wherein each dot represents a probe set, as described for example in U.S. Pat. No. 6,420,108, which is hereby incorporated herein in its entirety for all purposes. Typically, the dot's placement on the plot represents the intensity of the signal from hybridized, tagged, targets (as described in greater detail below) in one or more experiments. In these cases, a user may select a probe-set identifier by clicking on, drawing a loop around, or otherwise selecting one or more of the dots. In another example, user 275 may select a probe-set identifier by selecting a row or column in a table or spreadsheet that correlates probe sets with accession numbers and other genomic information.

Yet another type of probe-set identifier, as that term is used herein, includes a nucleotide or amino acid sequence. For example, it is illustratively assumed that a particular SIF is a unique sequence of 500 bases that is a portion of a consensus sequence or exemplar sequence gleaned from EST and/or genomic sequence information. It further is assumed that one or more probe sets are designed to represent the SIF. A user who specifies all or part of the 500-base sequence thus may be considered to have specified all or some of the corresponding probe sets.

As a further example with respect to a particular implementation, a user may specify a portion of the 500-base sequence noted above, which may be unique to that SIF, or, alternatively, may also identify another SIF, EST, cluster of EST's, consensus sequence, and/or gene or protein. The user thus specifies a probe-set identifier for one or more genes or EST's. In another variation, it is illustratively assumed that a particular SIF is a portion of a particular consensus sequence. It is further assumed that a user specifies a portion of the consensus sequence that is not included in the SIF but that is unique to the consensus sequence or the gene or EST's the consensus sequence is intended to represent. In that case, the sequence specified by the user is a probe-set identifier that identifies the probe set corresponding to the SIF, even though the user-specified sequence is not included in the SIF. Parallel cases are possible with respect to user specifications of partial sequences of EST's and genes or EST's, as those skilled in the relevant art will now appreciate.

A further example of a probe-set identifier is an accession number of a gene or EST. Gene and EST accession numbers are publicly available. A probe set may therefore be identified by the accession number or numbers of one or more EST's and/or genes corresponding to the probe set. The correspondence between a probe set and EST's or genes may be maintained in a suitable database from which the correspondence may be provided to the user. Similarly, gene fragments or sequences other than EST's may be mapped (e.g., by reference to a suitable database) to corresponding genes or EST's for the purpose of using their publicly available accession numbers as probe-set identifiers. For example, a user may be interested in product or genomic information related to a particular SIF that is derived from EST-1 and EST-2. The user may be provided with the correspondence between that SIF (or part or all of the sequence of the SIF) and EST-1 or EST-2, or both. To obtain product or genomic data related to the SIF, or a partial sequence of it, the user may select the accession numbers of EST-1, EST-2, or both.

Additional examples of probe-set identifiers include one or more terms that may be associated with the annotation of one or more gene or EST sequences, where the gene or EST sequences may be associated with one or more probe sets. For convenience, such terms may hereafter be referred to as "annotation terms" and will be understood to potentially include, in various implementations, one or more words, graphical elements, characters, or other representational forms that provide information that typically is biologically relevant to or related to the gene or EST sequence. Associations between the probe-set identifier terms and gene or EST sequences may be stored in a database such as a local genomic database, or they may be transferred from one or more remote databases. Examples of such terms associated with annotations include those of molecular function (e.g. transcription initiation), cellular location (e.g. nuclear membrane), biological process (e.g. immune response), tissue type (e.g. kidney), or other annotation terms known to those in the relevant art.

Figure 2:
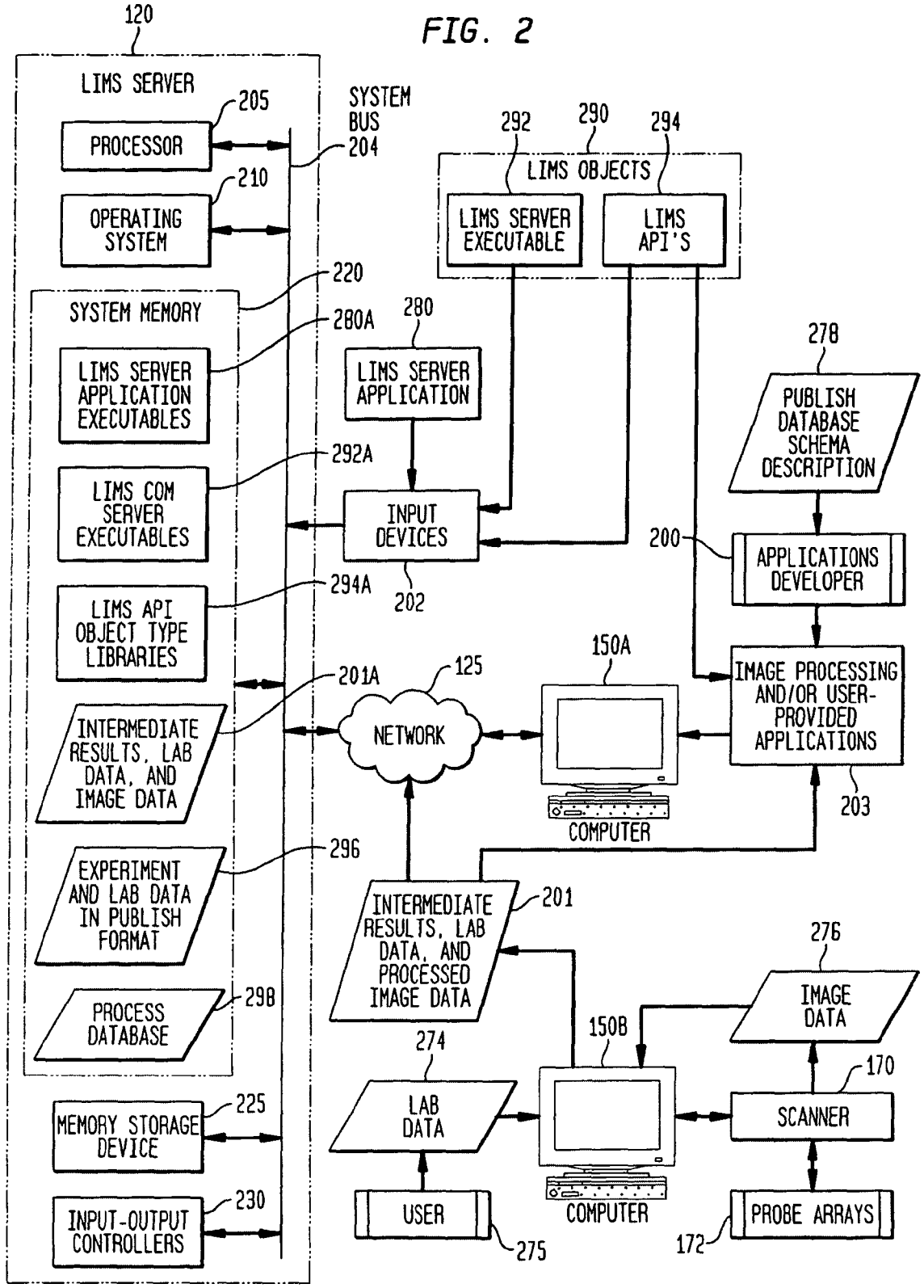
FIG. 2 is a functional block diagram of the laboratory information management system and user computers of FIG. 1 including illustrative embodiments of a scanner and hybridized probe arrays.

LIMS Server 120: FIG. 2 shows in greater detail a typical configuration of a server computer, such as server 120 of FIG. 1, coupled to a workstation computer via a network. For convenience, the server computer is referred to herein as LIMS server 120, although this computer may carry out a variety of functions in addition to those described below with respect to LIMS and LIMS-SDK software applications. Moreover, in some implementations any function ascribed to LIMS server 120 may be carried out by one or more other computers, and/or the functions may be performed in parallel by a group of computers. Network 125 may include a local area network, a wide area network, the Internet, another network, any combination thereof, or another computer system and network configuration.

Typically, LIMS server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as a processor 205, an operating system 210, a system memory 220, memory storage devices 225, and input-output controllers 230. It will be understood by those skilled in the relevant art that there are many possible configurations of the components of server 120 and that some components that may typically be included are not shown, such as cache memory, a data backup unit, and many other devices. Similarly, many hardware and associated software or firmware components that may be implemented in a network server are not shown in FIG. 2. For example, components to implement one or more firewalls to protect data and applications, uninterruptable power supplies, LAN switches, web-server routing software, and many other components are not shown. Those of ordinary skill in the art will readily appreciate how these and other conventional components may be implemented.

Processor 205 may include multiple processors; e.g., multiple Intel Xeon® 700 MHz. As further examples, processor 205 may include one or more of a variety of other commercially available processors such as Pentium® processors from Intel, SPARC® processors made by Sun Microsystems, or other processors that are or will become available. Processor 205 executes operating system 210, which may be, for example, a Windows®-type operating system (such as Windows® 2000 with SP 1, Windows NT® 4.0 with SP6a) from the Microsoft Corporation; the Solaris operating system from Sun Microsystems, the Tru64 Unix from Compaq, other Unix® or Linux-type operating systems available from many vendors; another or a future operating system; or some combination thereof. Operating system 210 interfaces with firmware and hardware in a well-known manner, and facilitates processor 205 in coordinating and executing the functions of various computer programs that may be written in a variety of programming languages. Operating system 210, typically in cooperation with processor 205, coordinates and executes functions of the other components of server 120. Operating system 210 also provides scheduling, input-output control, file and data management, memory management, and communication control and related services, all in accordance with known techniques.

System memory 220 may be any of a variety of known or future memory storage devices. Examples include any commonly available random access memory (RAM), magnetic medium such as a resident hard disk or tape, an optical medium such as a read and write compact disc, or other memory storage device. Memory storage device 225 may be any of a variety of known or future devices, including a compact disk drive, a tape drive, a removable hard disk drive, or a diskette drive. Such types of memory storage device 225 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 220 and/or the program storage device used in conjunction with memory storage device 225.

In some embodiments, a computer program product is described comprising a computer usable medium having control logic (computer software program, including program code) stored therein. The control logic, when executed by processor 205, causes processor 205 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via system bus 204. Some of these communications may be accomplished in alternative embodiments using network or other types of remote communications.

As will be evident to those skilled in the relevant art, LIMS server application 280, as well as LIMS Objects 290 including LIMS servers 292 and LIMS API's 294 (described below), if implemented in software, may be loaded into system memory 220 and/or memory storage device 225 through one of input devices 202. LIMS server application 280 as loaded into system memory 220 is shown in FIG. 2 as LIMS server application executables 280A. Similarly, objects 290 are shown as LIMS server executables 292A and LIMS API object type libraries 294A after they have been loaded into system memory 220. All or portions of these loaded elements may also reside in a read-only memory or similar device of memory storage device 225, such devices not requiring that the elements first be loaded through input devices 202. It will be understood by those skilled in the relevant art that any of the loaded elements, or portions of them, may be loaded by processor 205 in a known manner into system memory 220, or cache memory (not shown), or both, as advantageous for execution.

LIMS Server Application 280: Details regarding the operations of illustrative implementations of application 280 are provided in U.S. patent application Ser. Nos. 09/682,098 (hereby incorporated by reference herein in its entirety for all purposes) and 60/220,587, incorporated by reference above. It will be understood that the particular LIMS implementation described in this patent application is illustrative only, and that many other implementations may be used with LIMS objects 290 and other aspects of the present or alternative embodiments.

Application 280, and other software applications referred to herein, may be implemented using Microsoft Visual C++ or any of a variety of other programming languages. For example, applications may also be written in Java, C++, Visual Basic, any other high-level or low-level programming language, or any combination thereof.

As noted, certain implementations may be illustrated herein with respect to a particular, non-limiting, implementation of application 280, sometimes referred to as Affymetrix® LIMS. Full database functionality is intended to provide a data streaming solution and a single infrastructure to manage information from probe array experiments. Application 280 provides all the functionality of database storage and retrieval system for accessing and manipulating all system data. A database server provides an automated and integrated data management environment for the end user. All process data, raw data and derived data are stored as elements of the database, providing an alternative to a file-based storage mechanism. A database back end also provides integration of application 280 into a customer's overall information system infrastructure. Data is accessible through standard interfaces and can be tracked, queried, archived, exported, imported and administered.

Application 280 of the illustrated implementation, supports process tracking for a generic assay, adds enhanced administration functionality for managing GeneChip, spotted array, and AADM data (GeneChip data that has been published to the Affymetrix® Analysis Data Model standard), provides a full Oracle® database management software or SQL Server solution, supports publishing of genotype and sequence data, and provide a high level of security for the LIMS system. Aspects of illustrative publishing operations are described in U.S. patent application Ser. No. 09/683,982, which is hereby incorporated herein in its entirety for all purposes.

Application 280 of the illustrated example provides the following functionality. The Generic assay, supported by process tracking from enhancements to data management. The processes include but are not limited to the following: sample definition, experiment setup, hybridization, scanning, grid alignment, cell intensity analysis, probe array analysis, and publishing. The generic assay supports multiple experiments per sample definition via a re-queuing process, multiple hybridization and scan operations for a single experiment, data re-analysis, and publishing to more than one database. The Process Database, either an Oracle or SQL Server DBMS (Database management system) solution, fully supported by enhancements to CasoAffy (COM Communication layer to the process database). The GeneInfo Database, where enhancements provide additional support for storing chromosome and probe sequence information about the biological item on the probe array. The AADM Database, a database that stores the published GeneChip data, where enhancements provide full support for either an Oracle or SQL server DBMS. Additional tables to AADM provide support for genotype data, and modifications to the publishing components include data load performance improvements as well as bi-directional communication with GeneChip during publishing operations. The Security Database, a LIMS security database provides a role-based security level that is integrated with the Windows NT® user authentication security. The security database supports role definition, functional access within a role and assigning NT groups and users to those roles. A role is a collection of users, which have a common set of access rights to GeneChip data. Roles are defined per server/database and a role member can be a member of multiple roles, where the software determines a user's access rights. A function is a pre-determined action that is common to all roles. Each role is defined by the functions it can and cannot perform. Functions explicitly describe the type of action that a member of the role can perform. The functions supported by a newly created role includes but is not limited to the following: read process data, delete process data, update process data, archive process data, assume ownership of process data, import, export process data, delete AADM data, create a AADM database, and maintaining roles. When a new user is added to a role they will have access privileges for their data and read only access privilege for other user data within the same role. All non-role members are denied all access privileges to role member's data. When application 280 of the illustrated implementation is installed, at least two roles are created: administration and system user. The installer of the system software is added as a user to the administration role and a selected Windows NT® group is added as a user to the system user role. The LIMS Manager, which is a stand-alone application that provides user management capabilities for GeneChip® Analysis Suite data and AADM databases within the LIMS system. These capabilities include but are not limited to the following: AADM database creation, publish data deletion, process data deletion, taking ownership of process data, archiving and de-archiving of process data, data export, data import, role management, filter based find, managing expression analysis parameter sets, and managing sample and experiment attribution templates.

The system supports high volume reference and research labs that wish to manage and track laboratory workflow and GeneChip data, including DAT, EXP, CEL, CHP, CMP files that have been generated outside of the LIMS system, via a database. End users of the system include scientists, database administrators and system administrators.

LIMS Objects 290: LIMS Objects 290 is an optional object oriented programmers interface into LIMS server application 280. In the illustrated embodiment, LIMS objects 290 includes a number of Application Programmers Interfaces (APIs), generally and collectively represented as LIMS API's 294, and a number of LIMS servers, generally and collectively represented as LIMS servers 292. LIMS servers 292 may be distributed as out of process executables ("exe's") and LIMS API's 294 may be distributed as object type libraries ("tlb's"). It will be understood by those of ordinary skill in the art that various other distribution schemes and arrangements are possible.

LIMS Objects 290 typically may be used by an application developer (represented in FIG. 2 by applications developer 200) who wishes to integrate in-house or third-party software systems with a LIMS such as LIMS server application 280. For example, it is illustratively assumed that applications developer 200 works in an enterprise that employs LIMS server application 280 to manage data related to experiments conducted on probe arrays, which may include any type of probe arrays 172. It further is assumed for illustrative purposes that LIMS server application 280 is not a full-service system in that it does not provide functions such as laboratory process scheduling, sample management, instrument control, batch processing, and/or various data mining, processing, or visualization functions. Alternatively, application 280 may provide some or all of these functions, but applications developer 200 may wish to develop alternative or supplementary software applications to perform all or portions of any of these or other functions, and/or to integrate third-party software applications for these purposes. LIMS objects 290 provides developer 200 with tools to customize both the input of data into, and output of data from, LIMS server application 280.

LIMS objects 290 includes LIMS API's 294. API's 294, in a particular implementation of LIMS COM API's, includes the classes of loading list of objects, reading an object, updating/writing an object, deleting an object, processing data, creating AADM-compliant databases, and invocation of the analysis controller. API's are also included for objects, which are used by the previously listed classes.

Further aspects and implementations of the illustrated and other embodiments include the AADM database schema, which can be divided into four sub-schemas chip design, experiment setup, analysis results, and protocol parameters. The chip design sub-schema contains the overall chip description including the name, number of rows and columns of cells, the number of units, and a description of the units. The experiment setup sub-schema contains information on the chip used and the target that was applied. The analysis results sub-schema stores the results from any expression analysis. The protocol parameters sub-schema contains parameter information relating to target preparation, experiment setup, and chip analysis. The AADM database can be queried for analysis results, protocol parameters, and experiment setup in a similar fashion to the queries used by the Affymetrix® Data Mining Tool. The Affymetrix Data Mining Tool also uses a supplementary database called the Data Mining Info database, which stores user preferences, saved queries, frequently asked queries, and probe set lists. The Gene Info database, is used by Affymetrix® Microarray Suite, stores probe set information such as descriptions of probe sets, sequences that are tiled on an expression array, and user defined annotations. It also stores lists of external database links that allow users to add links to internal/external databases, which could be public or private.

Figure 3:
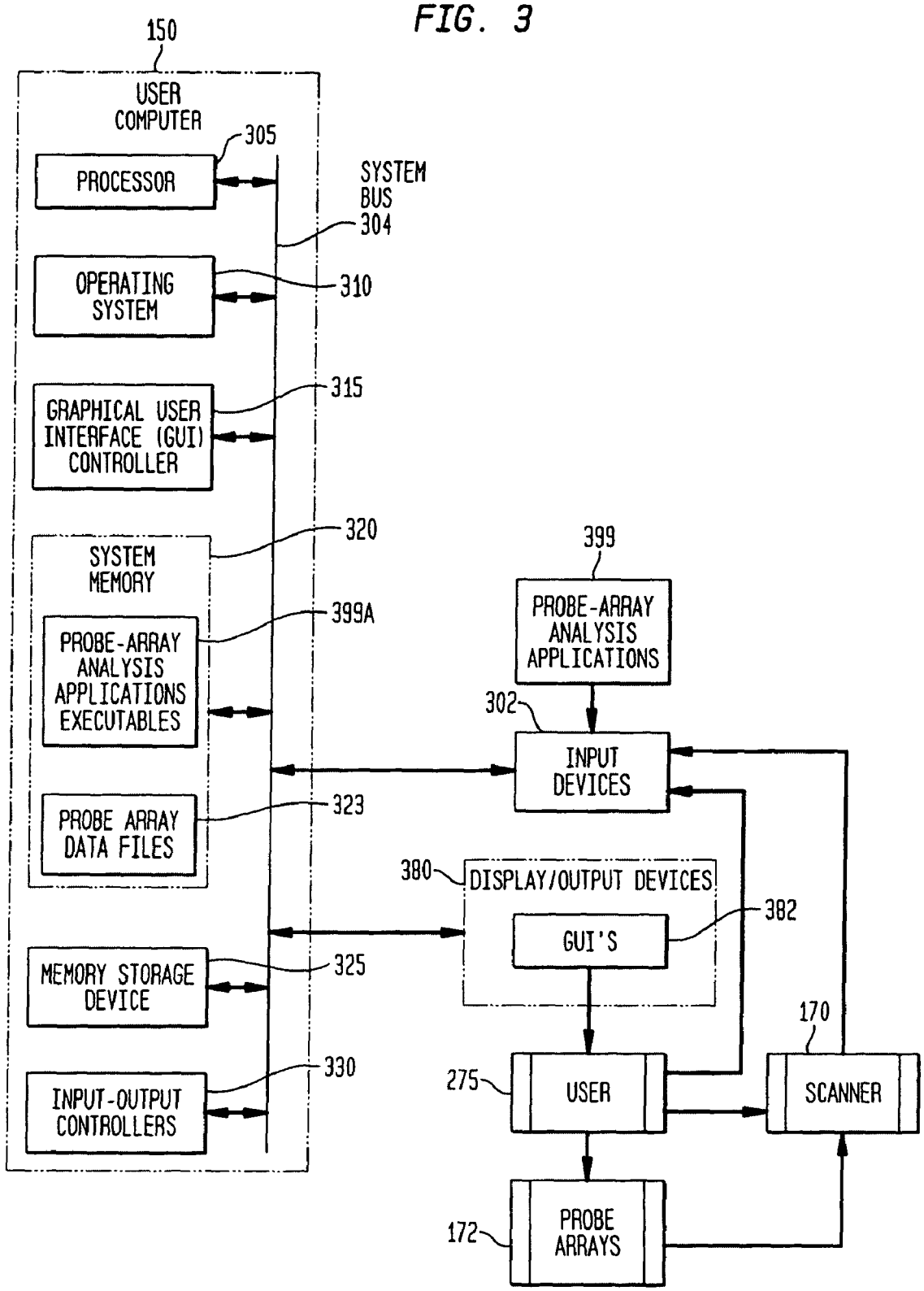
FIG. 3 is a functional block diagram of one implementation of a user computer system of FIGS. 1 and 2 including illustrative embodiments of probe-array analysis executables and display/output devices including graphical user interfaces.

FIG. 3 is a functional block diagram that shows in greater detail illustrative components of a scanner system 100 that, as shown in FIG. 1, may be coupled with LIMS server 120 via a network or otherwise. As noted, scanner system 100 includes a user computer 150 and scanner 170.

User Computer 150: User computer 150 may be a computing device specially designed and configured to support and execute some or all of the functions of probe array applications 399, described below. Computer 150 also may be any of a variety of types of general-purpose computers such as a personal computer, network server, workstation, or other computer platform now or later developed. Computer 150 typically includes known components such as a processor 305, an operating system 310, a graphical user interface (GUI) controller 315, a system memory 320, memory storage devices 325, and input-output controllers 330. It will be understood by those skilled in the relevant art that there are many possible configurations of the components of computer 150 and that some components that may typically be included in computer 150 are not shown, such as cache memory, a data backup unit, and many other devices. Processor 305 may be a commercially available processor such as a Pentium® processor made by Intel Corporation, a SPARC® processor made by Sun Microsystems, or it may be one of other processors that are or will become available. Processor 305 executes operating system 310, which may be, for example, a Windows®-type operating system (such as Windows NT® 4.0 with SP6a) from the Microsoft Corporation; a Unix® or Linux-type operating system available from many vendors; another or a future operating system; or some combination thereof. Operating system 310 interfaces with firmware and hardware in a well-known manner, and facilitates processor 305 in coordinating and executing the functions of various computer programs that may be written in a variety of programming languages. Operating system 310, typically in cooperation with processor 305, coordinates and executes functions of the other components of computer 150. Operating system 310 also provides scheduling, input-output control, file and data management, memory management, and communication control and related services, all in accordance with known techniques.

System memory 320 may be any of a variety of known or future memory storage devices. Examples include any commonly available random access memory (RAM), magnetic medium such as a resident hard disk or tape, an optical medium such as a read and write compact disc, or other memory storage device. Memory storage device 325 may be any of a variety of known or future devices, including a compact disk drive, a tape drive, a removable hard disk drive, or a diskette drive. Such types of memory storage device 325 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 320 and/or the program storage device used in conjunction with memory storage device 325.

In some embodiments, a computer program product is described comprising a computer usable medium having control logic (computer software program, including program code) stored therein. The control logic, when executed by processor 305, causes processor 305 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 330 could include any of a variety of known devices for accepting and processing information from a user, whether a human or a machine, whether local or remote. Such devices include, for example, modem cards, network interface cards, sound cards, or other types of controllers for any of a variety of known input devices 302. Output controllers of input-output controllers 330 could include controllers for any of a variety of known display devices 380 for presenting information to a user, whether a human or a machine, whether local or remote. If one of display devices 380 provides visual information, this information typically may be logically and/or physically organized as an array of picture elements, sometimes referred to as pixels. Graphical user interface (GUI) controller 315 may comprise any of a variety of known or future software programs for providing graphical input and output interfaces between computer 150 and user 275, and for processing user inputs. In the illustrated embodiment, the functional elements of computer 150 communicate with each other via system bus 304. Some of these communications may be accomplished in alternative embodiments using network or other types of remote communications.

As will be evident to those skilled in the relevant art, applications 399, if implemented in software, may be loaded into system memory 320 and/or memory storage device 325 through one of input devices 302. All or portions of applications 399 may also reside in a read-only memory or similar device of memory storage device 325, such devices not requiring that applications 399 first be loaded through input devices 302. It will be understood by those skilled in the relevant art that applications 399, or portions of it, may be loaded by processor 305 in a known manner into system memory 320, or cache memory (not shown), or both, as advantageous for execution.

Scanner 170: Scanner 170 of this example provides an image of hybridized probe-target pairs by detecting fluorescent, radioactive, or other emissions; by detecting transmitted, reflected, or scattered radiation; by detecting electromagnetic properties or characteristics; or by other techniques. These processes or techniques may generally and collectively be referred to hereafter for convenience simply as involving the detection of "emissions." Various detection schemes are employed depending on the type of emissions and other factors. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Illustrative scanners or scanning systems that, in various implementations, may include scanner 170 are described in U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,252,236; in PCT Application PCT/US99/06097 (published as WO99/47964); in U.S. patent application Ser. Nos. 10/063,284, 09/683,216, 09/683,217, 09/683,219, 09/681,819, and 09/383,986; and in U.S. Provisional Patent Application Ser. Nos. 60/364,731, and 60/286,578, each of which is hereby incorporated herein by reference in its entirety for all purposes.

Scanner 170 of this non-limiting example provides data representing the intensities (and possibly other characteristics, such as color) of the detected emissions, as well as the locations on the substrate where the emissions were detected. The data typically are stored in a memory device, such as system memory 320 of user computer 150, in the form of a data file. One type of data file, such as image data 276 shown in FIG. 2 that could for example be in the form of a "*.cel" file generated by Microarray Suite software available from Affymetrix, Inc., typically includes intensity and location information corresponding to elemental sub-areas of the scanned substrate. In the illustrated example of FIG. 2, data 276 could be received by computer 150C where a *.cel file could be generated or the *.cel file could be generated by scanner 170. Alternatively data 276 may be directly processed or some other uses of data 276 known to those of ordinary skill in the related art. The term "elemental" in this context means that the intensities, and/or other characteristics, of the emissions from this area each are represented by a single value. When displayed as an image for viewing or processing, elemental picture elements, or pixels, often represent this information. Thus, for example, a pixel may have a single value representing the intensity of the elemental sub-area of the substrate from which the emissions were scanned. The pixel may also have another value representing another characteristic, such as color. For instance, a scanned elemental sub-area in which high-intensity emissions were detected may be represented by a pixel having high luminance (hereafter, a "bright" pixel), and low-intensity emissions may be represented by a pixel of low luminance (a "dim" pixel). Alternatively, the chromatic value of a pixel may be made to represent the intensity, color, or other characteristic of the detected emissions. Thus, an area of high-intensity emission may be displayed as a red pixel and an area of low-intensity emission as a blue pixel. As another example, detected emissions of one wavelength at a particular sub-area of the substrate may be represented as a red pixel, and emissions of a second wavelength detected at another sub-area may be represented by an adjacent blue pixel. Many other display schemes are known. Various techniques may be applied for identifying the data representing detected emissions and separating them from background information. For example, U.S. Pat. No. 6,090,555, and U.S. patent application Ser. No. 10/197,369, titled "System, Method, and Computer Program Product for Scanned Image Alignment" filed Jul. 17, 2002, which are both hereby incorporated by reference herein in their entireties for all purposes, describe various of these techniques. In a particular implementation, scanner 170 may identify one or more labeled targets. For instance, sample of a first target may be labeled with a first dye (an example of what may more generally be referred to hereafter as an "emission label") that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probe arrays, and conditions may be created conducive to hybridization reactions, all in accordance with known techniques.

Probe-Array Analysis Applications 399: Generally, a human being may inspect a printed or displayed image constructed from the data in an image file and may identify those cells that are bright or dim, or are otherwise identified by a pixel characteristic (such as color). However, it frequently is desirable to provide this information in an automated, quantifiable, and repeatable way that is compatible with various image processing and/or analysis techniques. For example, the information may be provided for processing by a computer application that associates the locations where hybridized targets were detected with known locations where probes of known identities were synthesized or deposited. Other methods include tagging individual synthesis or support substrates (such as beads) using chemical, biological, electromagnetic transducers or transmitters, and other identifiers. Information such as the nucleotide or monomer sequence of target DNA or RNA may then be deduced. Techniques for making these deductions are described, for example, in U.S. Pat. No. 5,733,729, which hereby is incorporated by reference in its entirety for all purposes, and in U.S. Pat. No. 5,837,832, noted and incorporated above.

A variety of computer software applications are commercially available for controlling scanners (and other instruments related to the hybridization process, such as hybridization chambers), and for acquiring and processing the image files provided by the scanners. Examples are the Jaguar™ application from Affymetrix, Inc., aspects of which are described in PCT Application PCT/US 01/26390 and in U.S. patent application Ser. Nos. 09/681,819, 09/682,071, 09/682, 074, and 09/682,076, and the Microarray Suite application from Affymetrix, aspects of which are described in U.S. Provisional Patent Applications, Ser. Nos. 60/220,587, 60/220,645 and 60/312,906, all of which are hereby incorporated herein by reference in their entireties for all purposes. For example, image data in image data file 276 may be operated upon to generate intermediate results such as so-called cell intensity files (*.cel) and chip files (*.chp), generated by Microarray Suite or spot files (*.spt) generated by Jaguar™ software. For convenience, the terms "file" or "data structure" may be used herein to refer to the organization of data, or the data itself generated or used by executables 399A and executable counterparts of other applications. However, it will be understood that any of a variety of alternative techniques known in the relevant art for storing, conveying, and/or manipulating data may be employed, and that the terms "file" and "data structure" therefore are to be interpreted broadly. In the illustrative case in which image data file 276 is derived from a GeneChip® probe array, and in which Microarray Suite generates probe array intensity data file 440, file 440 may contain, for each probe scanned by scanner 170, a single value representative of the intensities of pixels measured by scanner 170 for that probe. Thus, this value is a measure of the abundance of tagged cRNA's present in the target that hybridized to the corresponding probe. Many such cRNA's may be present in each probe, as a probe on a GeneChip® probe array may include, for example, millions of oligonucleotides designed to detect the cRNA's. The resulting data stored in the chip file may include degrees of hybridization, absolute and/or differential (over two or more experiments) expression, genotype comparisons, detection of polymorphisms and mutations, and other analytical results. In another example, in which executables 399A includes image data from a spotted probe array, the resulting spot file includes the intensities of labeled targets that hybridized to probes in the array. Further details regarding cell files, chip files, and spot files are provided in U.S. Provisional Patent Application Nos. 60/220,645, 60/220,587, and 60/226,999, incorporated by reference above.

Figure 4:
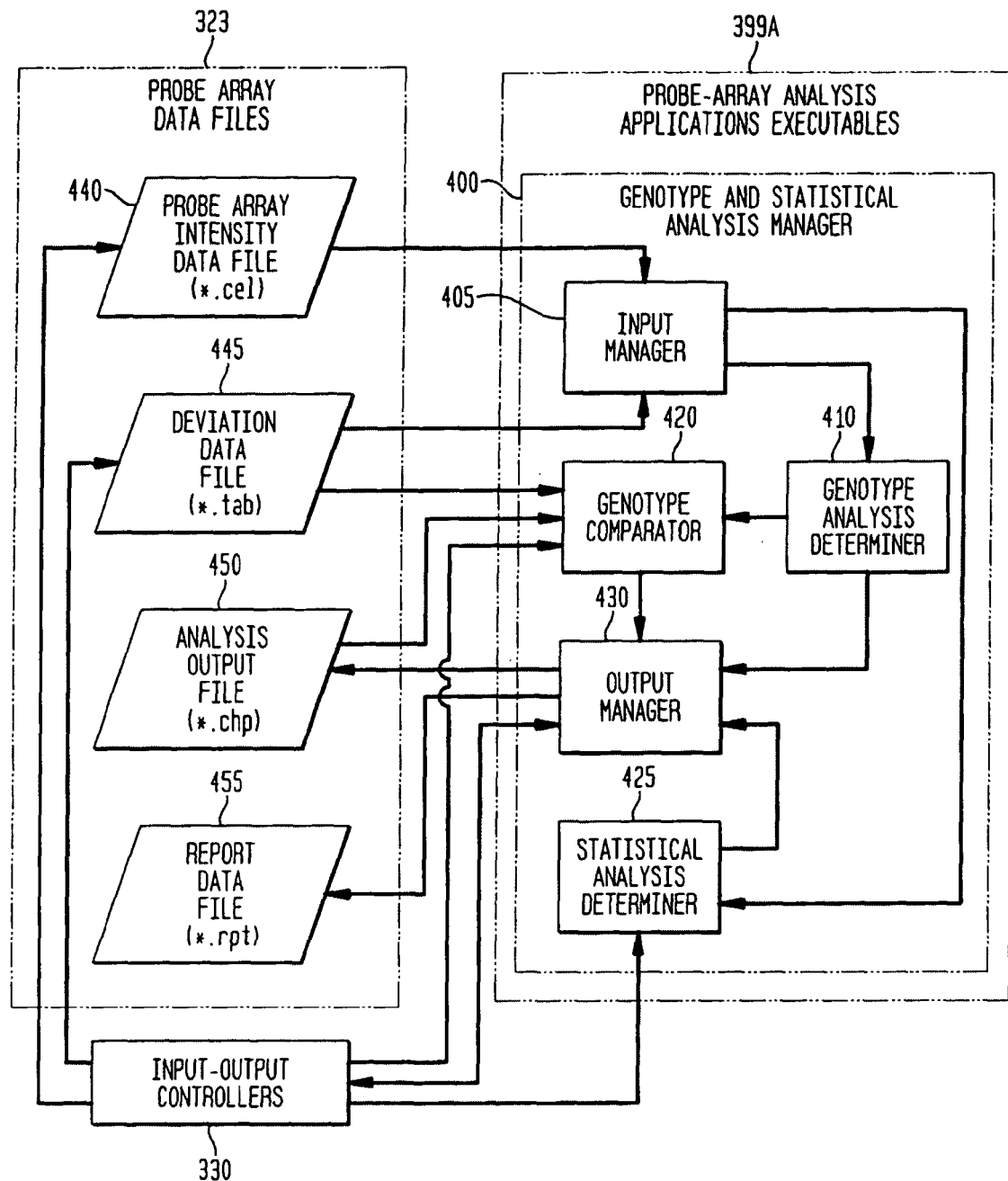
FIG. 4 is a functional block diagram of the probe-array analysis executables of FIG. 3 including one implementation of a genotype and statistical analysis manager.

In the present example, in which executables 399A include Affymetrix® Microarray Suite, the chip file is derived from analysis of the cell file combined in some cases with information derived from library files. A non-limiting example is illustrated in FIG. 4 as deviation data file (*.tab) 445 that specifies details regarding the sequences and locations of probes and controls. Laboratory or experimental data may also be provided to the software for inclusion in the chip file. For example, an experimenter and/or automated data input devices or programs may provide data related to the design or conduct of experiments. As a non-limiting example, the experimenter may specify an Affymetrix catalogue or custom chip type (e.g., Human Genome U95Av2 chip) either by selecting from a predetermined list presented by Microarray Suite or by scanning a bar code related to a chip to read its type. Also, this information may be automatically read. For example, a bar code (or other machine-readable information such as may be stored on a magnetic strip, in memory devices of a radio transmitting module, or stored and read in accordance with any of a variety of other known techniques) may be affixed to the probe array, a cartridge, or other housing or substrate coupled to or otherwise associated with the array. The machine-readable information may automatically be read by a device (e.g., a 1-D or 2-D bar code reader) incorporated within the scanner, an autoloader associated with the scanner, an autoloader movable between the scanner and other instruments, and so on. In any of these cases, Microarray Suite may associate the chip type, or other identifier, with various scanning parameters stored in data tables. The scanning parameters may include, for example, the area of the chip that is to be scanned, the starting place for a scan, the location of chrome borders on the chip used for auto-focusing, the speed of the scan, a number of scan repetitions, the wavelength or intensity of laser light to be used in reading the chip, and so on. Rather than storing this data in data tables, some or all of it may be included in the machine-readable information coupled or associated with the probe arrays. Other experimental or laboratory data may include, for example, the name of the experimenter, the dates on which various experiments were conducted, the equipment used, the types of fluorescent dyes used as labels, protocols followed, and numerous other attributes of experiments.

As noted, executables 399A may apply some of this data in the generation of intermediate results. For example, information about the dyes may be incorporated into determinations of relative expression. Other data, such as the name of the experimenter, may be processed by executables 399A or may simply be preserved and stored in files or other data structures. Any of these data may be provided, for example over a network, to a laboratory information management server computer, such as LIMS server 120 of FIGS. 1 and 2, configured to manage information from large numbers of experiments. A data analysis program may also generate various types of plots, graphs, tables, and other tabular and/or graphical representations of analytical data. As will be appreciated by those skilled in the relevant art, the preceding and following descriptions of files generated by executables 399A are exemplary only, and the data described, and other data, may be processed, combined, arranged, and/or presented in many other ways.

The processed image files produced by these applications often are further processed to extract additional data. In particular, data-mining software applications often are used for supplemental identification and analysis of biologically interesting patterns or degrees of hybridization of probe sets. An example of a software application of this type is the Affymetrix® Data Mining Tool, described in U.S. patent application Ser. No. 09/683,980, which is hereby incorporated herein by reference in its entireties for all purposes. Software applications also are available for storing and managing the enormous amounts of data that often are generated by probe-array experiments and by the image-processing and data-mining software noted above. An example of these data-management software applications is the Affymetrix® Laboratory Information Management System (LIMS). In addition, various proprietary databases accessed by database management software, such as the Affymetrix® EASI (Expression Analysis Sequence Information) database and database software, provide researchers with associations between probe sets and gene or EST identifiers.

For convenience of reference, these types of computer software applications (i.e., for acquiring and processing image files, data mining, data management, and various database and other applications related to probe-array analysis) are generally and collectively represented in FIG. 3 as probe-array analysis applications 399. FIG. 3 illustratively shows applications 399 stored for execution (as executable code 399A corresponding to applications 399) in system memory 320 of user computer 150.

As will be appreciated by those skilled in the relevant art, it is not necessary that applications 399 be stored on and/or executed from computer 150; rather, some or all of applications 399 may be stored on and/or executed from an applications server or other computer platform to which computer 150 is connected in a network. For example, it may be particularly advantageous for applications involving the manipulation of large databases to be executed from a database server such as user database server 120 of FIG. 1. Alternatively, LIMS, DMT, and/or other applications may be executed from computer 150, but some or all of the databases upon which those applications operate may be stored for common access on server 120 (perhaps together with a database management program, such as the Oracle® 8.0.5 database management system from Oracle Corporation). Such networked arrangements may be implemented in accordance with known techniques using commercially available hardware and software, such as those available for implementing a local-area network or wide-area network. A local network is represented in FIG. 2 by the connection of user computer 150 to user database server 120 (and to user-side Internet client 410, which may be the same computer) via a network cable, wireless network, or other means of networking known to those in the related art. Similarly, scanner 170 (or multiple scanners) may be made available to a network of users over a network cable both for purposes of controlling scanner 170 and for receiving data input from it.

In some implementations, it may be convenient for user 275 to group probe-set identifiers for batch transfer of information or to otherwise analyze or process groups of probe sets together. For example, as described below, user 275 may wish to obtain annotation information related to one or more probe sets identified by their respective probe set identifiers. Rather than obtaining this information serially, user 275 may group probe sets together for batch processing. Various known techniques may be employed for associating probe set identifiers, or data related to those identifiers, together. For instance, user 275 may generate a tab delimited *.txt file including a list of probe set identifiers for batch processing. This file or another file or data structure for providing a batch of data (hereafter referred to for convenience simply as a "batch file"), may be any kind of list, text, data structure, or other collection of data in any format. The batch file may also specify what kind of information user 275 wishes to obtain with respect to all, or any combination of, the identified probe sets. In some implementations, user 275 may specify a name or other user-specified identifier to represent the group of probe-set identifiers specified in the text file or otherwise specified by user 275. This user-specified identifier may be stored by one of executables 399A, so that user 275 may employ it in future operations rather than providing the associated probe-set identifiers in a text file or other format. Thus, for example, user 275 may formulate one or more queries associated with a particular user-specified identifier, resulting in a batch transfer of information from portal 400 to user 275 related to the probe-set identifiers that user 275 has associated with the user-specified identifier. Alternatively, user 275 may initiate a batch transfer by providing the text file of probe-set identifiers. In any of these cases, user 275 may provide information, such as laboratory or experimental information, related to a number of probe sets by a batch operation rather than serial ones. The probe sets may be grouped by experiments, by similarity of probe sets (e.g., probe sets representing genes having similar annotations, such as related to transcription regulation), or any other type of grouping. For example, user 275 may assign a user-specified identifier (e.g., "experiments of January 1") to a series of experiments and submit probe-set identifiers in user-selected categories (e.g., identifying probe sets that were up-regulated by a specified amount) and provide the experimental information to portal 400 for data storage and/or analysis.

Genotype and Statistical Analysis Manager 400: FIG. 4 is a functional block diagram of a particular implementation of probe-array analysis applications executables 399, referred to as executables 399A, that includes genotype and statistical analysis manager 400. As noted, manager 400 provides a user with information related to results from experiments with probe arrays. In the illustrated implementation, manager 400 includes input manager 405, genotype analysis determiner 410, statistical analysis determiner 425, genotype comparator 420, and output manager 430. The function and purpose of each component will be described in detail below. It should be understood that the functions of these elements may be distributed and/or combined among them in numerous variations and that not all functions need be present in alternative implementations. For example, the functions of input manager 405 and/or output manager 430 could be performed by one or both of comparator 420 or determiner 410. Similarly, the functions of determiner 410 and comparator 420 could be performed by either alone in other implementations, or otherwise distributed. Thus, generally, functions are assigned to the elements described below for purposes of clarity with respect to the illustrated implementation, but these descriptions should be understood to be to be non-limiting.

One function of input manager 405 in the illustrated implementation is to receive one or more sets of data from probe array data files 323 and provide the one or more sets of data to the appropriate elements of manager 400. The data could include probe array intensity data file (e.g., *.cel) 440 that could include image data 276, deviation data file (e.g., *.tab) 445, or other types of data that could include various library or experiment files. Another function of the illustrated implementation of manager 405 is to determine where to direct the one or more data files that may include multiple data files of the same type. For example, two probe array intensity data files 440 may be processed by input manager 405 for the purpose of determining differences in genotype calls. Manager 405 may direct data from both files, as well as additional library or experiment files as appropriate, to genotype analysis determiner 410 (discussed further below).

Additionally, input manager 405 may distinguish between files that correspond to different types of probe arrays but may be of the same data file type, e.g., instances of data file 440 from experiments with different types of probe arrays. Manager 405 may determine the probe array type from analysis of the intensity data file by, for example, comparing features of the file to a template or look-up table of fiducial features. Probe array types could include those designed for genotype analysis, expression analysis, or other type of analysis. Alternatively, manager 405 could identify the probe array types by consulting additional data files including experiment files, library files, or some other means of identification in accordance with techniques known to those of ordinary skill in the related art. In a particular implementation, input manager 405 receives first emission intensity data and second emission intensity data corresponding to probes disposed upon a biological probe array and directs this data to genotype analysis determiner 410 and/or statistical analysis determiner 425 for processing as described below.

Also illustrated in FIG. 4 is genotype analysis determiner 410 that, in some implementations, determines first and second genotype calls for one or more probe sets based, at least in part, on the first and second emission intensity data provided by input manager 405. Thus, determiner 410 analyzes results from probe arrays designed specifically to interrogate particular regions of a genome that may include what are referred to as a single nucleotide polymorphisms (hereafter referred to as SNP's), or other features known to those of ordinary skill in the relevant art that could be used for genotyping. Generally speaking, a SNP is a single base pair difference within a DNA sequence that is different from what is the most commonly identified base in a sequence from a population. A SNP is commonly defined to occur at a frequency that is greater than one percent of the population. An occurrence of less than one percent is commonly referred to as a mutation, thus a SNP is a more common event in a population than a mutation. The term "population" as used here commonly refers to the general known population, although it could be used to refer to smaller groups that may be separated by ethnicity, geographical location, or some other distinction. Each probe set on the probe array may, for example, be designed to interrogate a particular "biallelic" SNP. The term "biallelic" refers to a state where there are two possible bases for that SNP (what are commonly referred to as the consensus and the polymorphic base) and each is referred to as an allele, typically represented as the A allele and the B allele. As an alternative example, the probe array could be designed to interrogate "multiallelic" sequences that could be related to what are referred to by those in the art as microsatellites, or other situations where more than two possible alleles exist. The term "interrogate" is used broadly to mean that the probe set is designed to determine which of alternative nucleotides is present in a particular sample, e.g., to distinguish a "G" from a "C" in a particular position.

Generally each probe set is designed to interrogate a different SNP, although an exception is the case in which two probe sets are designed to interrogate both the coding strand of DNA, known as the sense strand, and the complementary non-coding strand, known as the anti-sense strand, for the same SNP. A probe set may also be referred to as a BLOCK of probes where, for example, two or more probes within the BLOCK may interrogate the same DNA sequence except for the SNP base position. For example a pair of probes may be designed to interrogate the A and B alleles of the SNP respectively and may be referred to for convenience of reference as a miniBLOCK.

A BLOCK may be comprised of a plurality of miniBLOCKS that each are designed to interrogate the same SNP but may differ in the exact sequence to be interrogated. For instance, one miniBLOCK may interrogate the SNP position at the centermost position of the probe sequence, and a different miniBLOCK may interrogate the SNP position at one of the ends of the probe sequence. The result is that the probe sequences may differ from one another slightly between miniBLOCKS. As a further example, the miniBLOCK could consist of four probes where two probes are designed to interrogate the A allele and two for the B allele. In the present example, one of the probes from the A allele pair and one from the B allele pair may interrogate a perfect match to the desired DNA sequence. The other may be designed to interrogate a mismatch that could be a similar sequence to the perfect match probe with one or more base pair differences at one or more different positions in the probe. The combination of the perfect match and the mismatch probes in addition to the number and sequence composition of miniBLOCKS could further be used to determine the hybridization efficiency or some other experimental aspect that may increase the accuracy of genotype calls. Additional examples of genotyping probe arrays are described in PCT Application No. WO 95/11995, which is hereby incorporated by reference herein in its entirety for all purposes.

In an illustrated implementation, file 440 contains emission intensity values corresponding to each probe of every probe set disposed upon a single probe array. As noted above with respect to an illustrative implementation, the intensity values generally represent the degree of hybridization, or not, of a probe with a labeled target. Determiner 410 analyzes the emission intensity value for each probe of a probe set and makes a call for the probe set where the call may include a genotype determination. The genotype determination call may include assigning a quantitative representation of the intensity values for the probe set, referred to as the relative allele signal (hereafter referred to for convenience as the "RAS"). The value of the RAS, for example, may correspond to the allele of the base located at the SNP position and on that basis may be assigned a qualitative genotype call as either A, B, or AB. In the present example, the call may thus be indicative of either a homozygous or heterozygous condition, as will be discussed further below in relation to comparator 420.

In the illustrated implementation determiner 410 generates analysis information including, but not limited to, probe array data, RAS data for each probe set, and a qualitative call for each probe set. This information, as processed for formatting or other purposes in this implementation by output manager 430, may be stored in analysis output file 450. As non-limiting examples, output manager 430 may also process this information for storage in one or more databases, presented to the user within a GUI, and/or directed to genotype comparator 420. Examples of data stored in output file 450 are described later in reference to output manager 430.

As noted, manager 400 of the illustrated implementation also includes genotype comparator 420 that compares first genotype calls with corresponding second genotype calls (e.g., where the calls are made by determiner 410) and with a reference value. For example, comparator 420 in some implementations identifies probe sets in which a different genotype call has been made between two experimental conditions that could relate to what is referred to by those of ordinary skill in the relevant art as loss of heterozygosity. Loss of heterozygosity is a characteristic associated with several types of cancer where a normal tissue may be heterozygous in specific genes and a cancer tissue may be homozygous in the same genes. A gene typically exists as two copies (there are cases where more than two copies exist). Typically there is one copy of a gene on each chromosome of a pair (chromosomes typically occur in pairs in eukaryotes), but the copies are not always exactly the same in which case each unique copy is referred to as an allele. An allele may function normally, or the allele may either lose or gain a function with the consequence that cell processes are disrupted and potentially detrimental effects ensue. As is known to those of ordinary skill in the relevant art, if both copies have the same allele the gene is in a homozygous state, e.g., represented as "AA" or "BB." Alternatively, if there are two different alleles, the gene is in a heterozygous state, e.g., represented as "AB." In cases in which a particular allele functions abnormally, there may be little or no effect if it is paired with a normal functioning allele in the heterozygous state. But if there a two alleles with abnormal function in the homozygous state, there could be deleterious effects. It is also possible to have two normally functioning alleles in a homozygous state, so a homozygous state is not necessarily a sign of deleterious effects.

In the illustrated implementation, genotype comparator 420 may receive information from a plurality of output files 450 that correspond to the same probe array type. Comparator 420 may also receive information from one or more library files from probe array data files 323 or other source that could include input manager 405. For example, a library file could include deviation data file 445 that contains experimentally derived standard deviation values for each probe set of the probe array type corresponding to files 450.

Comparator 420 compares the genotype call results from determiner 410 for each probe set on a first probe array against the results for the corresponding probe set on one or more second probe arrays. For example, comparator 420 may receive information from two output files 450 files that could be the results from scanned HuSNP™ probe arrays from Affymetrix, Inc. The probe arrays are identical in probe set composition and order, but have been exposed to two different experimental samples. File 445 in this example includes standard deviation values for each of the probe sets on the probe array to address experimental differences that may be unique to each probe set. In the present example, analysis output files 450 may have been created at the same time or at times that may differ by large time periods. For instance a file 450 may have been created from a tissue sample from an area of skin at one time, and the second may have been created years later from the same area of skin. For instance the second sample could be from an area that may be presumed to have developed skin cancer where the two files could then be directly compared so that a potentially detrimental loss of heterozygosity in one or more critical genes could be identified.

Figure 5A:
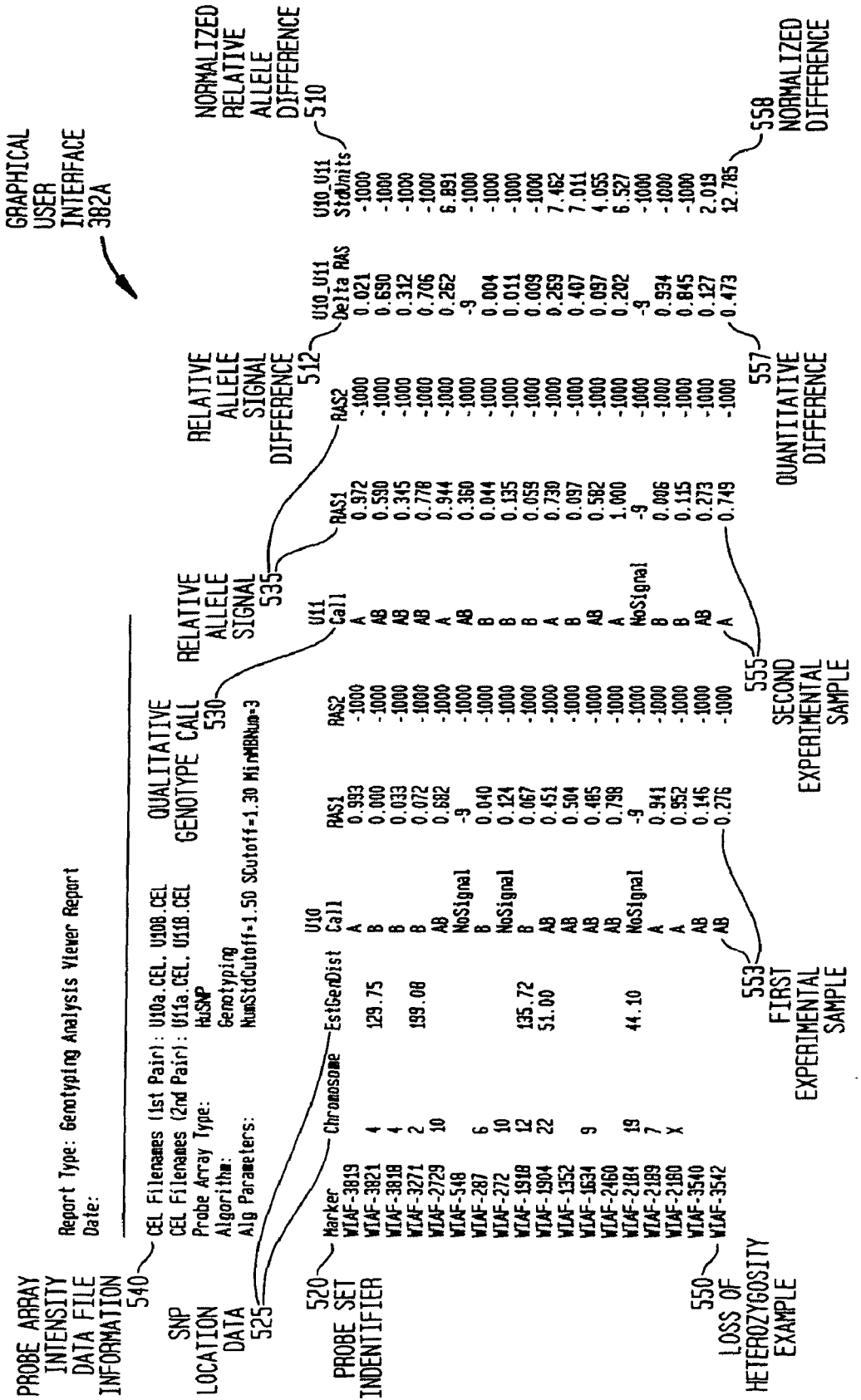

Returning to the present implementation, the quantitative genotype call values are compared between the two files, along with a reference value from the standard deviation file, to generate a quantitative value for the change in RAS, referred to hereafter as normalized delta RAS. The standard deviation file contains reference values that are representative of the variation that is specific to each probe set. The reference values may be experimentally derived from one or more sets of data or by some other method where a specific value may be applied to each probe set independently. The reference values could also be modified or completely replaced by user selected values. The reference value may be used to normalize the value of delta RAS that corresponds to the same probe set. The term "normalize" as used herein refers to a mathematical or other process to account for variation between samples that in this case may apply to variation between intensity values of probe sets. Variations could be caused by factors such as the influence of flanking sequences, and numerous other sources known to those of ordinary skill in the relevant art. Examples of normalized delta RAS are illustrated in FIG. 5A as normalized relative allele signal difference 510. The column associated with signal difference 510 has quantitative values for normalized delta RAS related with the probe set associated with each row. In some cases a probe set may not have a normalized relative allele difference 510 value associated with it. This could be the result of a variety of factors including the lack of a reference value to be used for normalization, some user selectable parameter, or other reason for the omission of a significant value. If no value is associated with difference 510, a value of "–1000" as shown in this example, or any other value or symbol in other implementations, may be displayed in the column. Also in the present implementation, there may be a column to display non-normalized RAS in addition to or instead of the normalized RAS column. An example of the non-normalized RAS column is illustrated in FIG. 5A as relative allele signal difference 512.

The value of delta RAS may be calculated by a variety of methods. One method includes implementing the following equation:

$$\text{Delta RAS} = |\text{RAS sample 1} - \text{RAS sample 2}|$$

Delta RAS represents the absolute value of the difference between the RAS from the first sample and the RAS from the second sample. The term "absolute value" as used herein may be the distance from zero or a positive reference value. The absolute value of the difference will yield a non-negative number, so if the RAS from sample 2 is a larger number than the RAS from sample 1 then the delta RAS will still be a positive number representing the degree of difference between the two values.

In the present example the reference standard deviation value may be incorporated into the calculations with the following equation:

$$\text{Normalized Delta RAS} = (\text{Delta RAS})/(\text{Probe Set Standard Deviation})$$

Delta RAS could represent change in either direction such as a loss of heterozygosity (i.e. going from an AB genotype to AA or BB), or a gain of heterozygosity (i.e. going from AA or BB to AB). This information may be presented to a user using an interface such as illustrative GUI 382A of FIG. 5A. For instance, loss of heterozygosity example 550 involving probe set WIAF-3542 is identified in the column labeled as probe set identifier 520. Example 550 has a qualitative genotype call of AB and corresponding quantitative RAS of 0.276 in first experimental sample 553. The genotype call changes to an A genotype call (an abbreviation of a homozygous AA genotype call) in second experimental sample 555 and has an associated RAS value of 0.749. The change between sample 553 and sample 555 is represented by quantitative difference 557 in the relative allele signal difference 512 column having an associated value of 0.473, and a normalized difference 558 of 12.785. The values for normalized relative allele signal difference 510 and relative allele signal difference 512 may represent a shift in signal from a heterozygous call towards a homozygous call of either of the alleles, or alternatively from a homozygous call of either of the alleles towards a heterozygous call. Difference 510 and 512 may also represent cases in which there has been no change in the genotype calls. The shift in genotype call may be based on a numerical threshold value applied to the difference 510. For instance the threshold value in the present example could be 0.2, where the value of 0.516 illustrated by difference 557 is above the 0.2 threshold value and thus confirms that the genotype call has changed. Values below the threshold value may be disregarded as experimental variation and called as no change in genotype.

Relative allele signal 535 may be comprised of RAS1 and RAS2 as illustrated in FIG. 5A, where RAS1 may correspond to a probe set that interrogates the coding strand of DNA. RAS2 may be a probe set designed to interrogate the non-coding strand, an additional copy of the same gene that may include one or more different alleles, or other sequence that may assist in the determination of the genotype of the particular gene represented by RAS1. As illustrated in FIG. 5A, there may not always be a probe set that corresponds to RAS2 and entries in this column may therefore be assigned a value of –1000 or other value, indicator, or symbol that indicates that absence of a corresponding probe set. Alternatively when RAS 2 has an associated probe set, RAS2 may have a value similar to that of RAS1 that represents a genotype call for the interrogated sequence. An algorithm may be used that includes both RAS1 and RAS2 for the determination of a value in the qualitative genotype call 530 column. For example, the algorithm could include the average RAS value for RAS1 and RAS2. The equation for the calculation may include:

$$\text{RAS sample} = (\text{RAS1} + \text{RAS2})/2$$

The algorithm could also weight one of the values higher than the other. For instance RAS1 may be weighted more heavily than RAS2 because it corresponds to the coding strand of DNA. Also, the use of the reference values may be different when there are two probe sets RAS1 and RAS2. For example, the following equation could be used in the calculation for normalized delta RAS:

$$\text{Normalized Delta RAS} = (\text{Delta RAS}) / \sqrt{(\text{Std.dev1})^2 + (\text{Std.dev2})^2}$$

Where Std. dev 1 is the standard deviation value for the first probe set, and Std. dev 2 is the standard deviation value for the second probe set. The standard deviation values in this example may account for variability between probe sets that could be caused by factors such as differences in the sequence composition of the DNA sequence that neighbors the probe set target sequence.

It will be understood that the preceding equations and algorithms are illustrative only, and that other statistical representations known to those of ordinary skill in the relevant art may be used in alternative implementations. Further examples of genotyping methods using relative allele signals are described in U.S. patent application Ser. No. 09/758,872 that is hereby incorporated by reference herein in its entirety for all purposes.

In the illustrated implementation, comparator 420 generates information that is stored by output manager 430 in report data file 455. File 455 contains the delta RAS results for each probe set along with other probe set related information that could include data from probe array intensity data file 440 and analysis output file 450. Alternatively, comparator 420 may filter the data included in data file 455, based on one or more parameters provided by user 275 and as discussed further in relation to graphical user interface 382B of FIG. 5B.

Output manager 430 may, in some implementations, display a measure of normalized change between the first and second genotype calls based, at least in part, on a comparison of first and second genotype calls and reference value. More specifically, with respect to an illustrative implementation, comparator 420 directs report data file 455 to output manager 430 where it may be stored in one or more databases such as probe array data files 323 and/or displayed to user 275 via a graphical user interface. Report data file 455 may also be compared to data files from one or more databases to correlate the changes in genotype calls with other specific signatures that may relate to a potential disease. For example, some loss of heterozygosity in some genes may have no detrimental effect, while in others the effect could be significant. Also, particular combinations of genes that have demonstrated a loss of heterozygosity could demonstrate the existence of, or a predisposition to, a disease condition such as cancer. The report file may be used to make a comparison against databases with disease data profiles and report back a diagnostic quantitative and/or qualitative call. Such database comparisons could be at the level of probe set, or could be a collective comparison of genotype calls (e.g., a haplotype analysis) that may be used, among other things, for population-based association studies.

In addition to the implementations involving genotype analysis described above, manager 400 in some embodiments includes functional elements for providing statistics-based expression analysis. For example, manager 400 may include statistical analysis determiner 425 that determines absolute or relative expression values based, at least in part, on a statistical measure of the emission intensity data and at least one user-selectable statistical parameter. In these implementations, output manager displays the absolute or relative expression values based, at least in part, on at least one user-selectable display parameter. For example, statistical analysis determiner 425 may use specific statistical algorithms designed to analyze emission intensity values from files derived from scanned probe arrays that test the expression of mRNA in an experimental sample, such as *.cel files from Affymetrix® GeneChip® probe arrays designed for expression analysis. Determiner 425 may perform a single-file analysis that evaluates the emission intensity values for each probe of a probe set on a single probe array and generates a detection p-value. The p-values for each probe of a probe set are further evaluated to make a detection call that corresponds to an mRNA transcript and that includes a present, absent, or no call. For example, a p-value close to zero may in some implementations be called as transcript present, whereas a p-value near 1 would be called as transcript absent.

Determiner 425 may also perform multiple-file analysis in order to determine the change of expression level of mRNA transcripts. In such an analysis, a p-value is generated that may be evaluated to make a change of expression call that, for example, could include an increase, decrease, or no change call. As used in this context, the term "p-value" refers to a measure of likelihood of a change of direction. For example, p-values close to 0.0 may indicate a high likelihood for an increase, values near 1.0 may indicate a high likelihood for a decrease, and values near 0.5 may indicate a weak likelihood for change in either direction.

Determiner 425 may receive user-selected parameters directly from input-output controllers 330 or as part of a data file from input manager 405. The user-selected parameters could be used in an algorithm, such as the One-Sided Wilcoxon's Signed Rank Test, for the calculation of the p-value to increase or decrease the sensitivity and/or specificity of the p-value. It will be understood that this test is a non-limiting example, and that other statistical tests or measures may be used in other implementations. For example, the user may choose to change a threshold value based on observed or calculated experimental variation or other criterion. More specifically in the present example of the p-value ranges noted above, the user may increase a threshold value above a small positive number such as 0.015. If raised, the threshold number may reduce the number of false present calls, but could also reduce the number of true present calls. Examples of statistical tests and algorithms are described further in U.S. patent application Ser. No. 09/735,574, which is hereby incorporated by reference herein in its entirety for all purposes.

Other user-selected parameters could include those used for the evaluation of the p-value in order to make a detection, change, or other type of call. For example, for a p-value that has a range between 0 and 1, the boundaries between calls could be 0.4 and 0.6 where p-values below 0.4 could be called as present, between 0.4 and 0.6 could be called as no call, and higher than 0.6 could be called as absent. In the present example, the user-selectable parameters could include the boundaries, in which case adjusting the values higher or lower could affect the sensitivity and/or specificity of the call. Further descriptions of the statistical algorithms and associated calls are described in U.S. patent application Ser. No. 09/758,872, which is hereby incorporated by reference herein in its entirety for all purposes.

In the illustrated implementation, output manager 430 receives data files from a plurality of sources such as genotype analysis determiner 410, genotype comparator 420, or statistical analysis determiner 425, and may save them in one or more databases that could be local or remote. For example, manager 430 may save a data file directly into probe array data files 323 or some other local location in addition to or instead of data files 323. Also, manger 430 may direct data files to remote databases through input-output manager 330. The remote databases may be located on LIMS server 120 connected by network 125 or some other remote database connected by the same or another network or by other methods known to those of ordinary skill in the art.

Output manager 430 may also direct data files to display/output devices 380 via input-output controllers 330 where the data files may be converted to GUI's 382 to be displayed to user 275. Illustrative examples of GUI's 382 from converted data files are presented in FIGS. 5A, 5B, and 6 as graphical user interfaces 382A, 382B, and 382C. GUI's 382 are comprised of graphical elements that in this illustrative and implementation that are constructed such that the data is presented in vertical columns and/or horizontal rows. More generally, GUI's 382 could be comprised of any graphical, text, or other format constructed to illustrate associations, relationships, and/or differences with color, columns/rows, or other method in accordance with known techniques or those that may be developed in the future. For example, illustrated in FIG. 5A is probe set identifier 520 in which a list of probe sets is arranged in a vertical column. The data that corresponds to an individual probe set is arranged in a horizontal row such as is illustrated as loss of heterozygosity probe set 550. In the present example, the probe set identifier is located on the far left. Along the row to the right there are columns that include SNP location data 525, genotype calls 530 and relative allele signals 535 for each experimental sample, and relative allele signal difference 510. The columns in each row contain data that correspond to each probe set listed in that row. Another element of interface 382A has a number includes, but is not limited to, probe array intensity data file information 540 that may provide information from one or more sets of data that could include probe array intensity data 540. For example, SNP location data 525 displays to the user the chromosome number and the estimated genetic distance from the SNP to the top of the short arm of the chromosome. The estimated genetic distance may be expressed as the number of bases, or in a preferred implementation in centimorgans. As is known by those of ordinary skill in the relevant art, a centimorgan may be defined as a unit of measure of recombination frequency. One centimorgan is equal to a 1% chance that a marker at one genetic locus will be separated from a marker at a second locus due to crossing over in a single generation. For example, in human beings, 1 centimorgan is equivalent, on average, to 1 million base pairs. Data 525 could also display relative distances to the next closest SNP, centromere, or other feature located on a chromosome.

Output manager 430 may also perform output and results filtering in some implementations. For example, manager 430 may receive user inputs to select specific parameters for sorting or displaying specific information based at least in part upon the input parameters. Some of the filtering operations or other processes that include user selected parameters could also be performed by comparator 420 or determiner 425.

FIG. 5B illustrates an additional example where the user may filter the results according to specific parameters. Graphical user interface 382B is an example in which the user has selected to filter the results based on a change of relative allele signal difference 512 column. as indicated by the differences in qualitative genotype call 530 where the call changes from a heterozygous call to a homozygous call for either allele type. Only those probe sets and the corresponding data in the same row that satisfy the criteria are a part of the filtered data set. Also the user may select which columns to view or delete from view, for example graphical user interface 382B of FIG. 5B illustrates a limited number of columns where the user may have designated the number and or composition of the columns.

The user-selected criteria may be received by comparator 420 from input-output controllers 330 so that the user may dynamically input different criteria in response to viewing interface 382B. Alternatively, the user-selected criteria could be included in deviation data file 445 or other data file that could include library or experiment data files that are directed to comparator 420. In the present example, comparator 420 (typically, as with determiner 410, by passing information to output manager 430) creates analysis output file 450 that contains only the filtered data. One benefit is that the size of the data file may be reduced so that data management is simplified with only data that is relevant to the user's experimental needs.

The filtering of data that results in a graphical user interface such as interface 382B of FIG. 5B could also be performed by output manager 430 on an unfiltered data file. For example, manager 430 may receive information needed to generate report data file 455 from comparator 420 and the user-selected parameters from input-output controllers 330 in order to perform the filtering operation. Manager 430 filters the data within data file 455 based upon the user-selected parameters and displays the filtered results in interface 382B. Manager 430 could create a new data file to store the filtered results in one or more data structures that could be the same or different file type as data file 455. In the present example, original data file 455 may remain unchanged where the user may recall data file 455 in order to filter by other parameters, display all of the data contained in the unfiltered data file, or use for the purposes of comparison with one or more other data files. Any of numerous conventional techniques may be employed to implement these and other filtering operations.

FIG. 6 is yet another illustrative example of a GUI for the display of analysis results in which graphical user interface 382C is a display of one possible result from statistical analysis determiner 425. Graphical user interface 382C is an example of the results from a detection call algorithm where the detection call includes a qualitative and quantitative value for each probe disposed upon a single probe array. Detection call 620 is a column where the qualitative detection call results may be displayed. The call may be based at least in part upon the quantitative value shown as P-value 630 that, in turn, may be based at least in part upon emission intensity data 625. In the present example the call could include "present," "absent" or "no call" depending at least in part upon the p-value that is representative of the level of detected expression for each mRNA molecule corresponding to a particular probe set. GUI 382C, and numerous variations thereof, may also be used to display other results from determiner 425, such as the detection of the change of expression when comparing the probe sets from two experiments that tested different sample on the same probe array type. Similarly, the results displayed in the call 620 column are based upon p-value 630. As with respect to GUI's 382A and 382B, the relationships indicated in GUI 382C using geometric arrangement (e.g., rows and columns in this example) could be implemented in numerous other ways in other implementations. For example, graphical elements indicating detection call and/or p value could be associated with probe set identifiers by using graphical plots in one, two, or three dimensions (e.g., scatter plots, histograms, and many other arrangements); arrows, edges, or other graphical indicators of relationships; or commonality of qualities such as color, shade, intensity, and so on. Thus, GUI's 382 should be considered as non-limiting examples of techniques for indicating relationships among values, and/or the values themselves, in an interface accessible by a user. Audio, video, and other media, in various combinations or alone, may also be used to indicate these relationships and/or values to a user.

Further aspects of processing probe array data to generate genotyping calls and measurements are described in a U.S. patent application Ser. No. 10/219,503, titled "System, Method, and Computer Software for Genotyping Analysis and Identification of Allelic Imbalance," filed concurrently herewith and hereby incorporated by reference herein in its entirety for all purposes.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments. For example, some or all of the functions described as being carried out by determiner 410 could be carried out by comparator 430, or these functions could otherwise be distributed among other functional elements. Also, the functions of several elements may, in alternative embodiments, be carried out by fewer, or a single, element. For example, the functions of determiner 410 and comparator 420 could be carried out by a single element in other implementations. Similarly, in some embodiments, any functional element may perform fewer, or different, operations than those described with respect to the illustrated embodiment. Also, functional elements shown as distinct for purposes of illustration may be incorporated within other functional elements in a particular implementation. For example, the functions performed by the two computers could be performed by a single server or other computing platform, distributed over more than two computer platforms, or other otherwise distributed in accordance with various known computing techniques.

Also, the sequencing of functions or portions of functions generally may be altered. Certain functional elements, files, data structures, and so on, may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. It further will be understood that references herein to such terms as "file," "data structure," or "database" are illustrative only and that, in various implementations, data described as being stored in a "file" may alternatively be stored in a database or otherwise stored in accordance with techniques and conventions familiar to those of ordinary skill in the relevant art or in accordance with techniques that may be developed in the future. Data stored in files, databases, or other structures or in accordance with other techniques may be stored locally and/or may be stored remotely, e.g., data may be distributed over a number of local and/or remote files or databases. Databases may be flat, relational, object oriented, or structured in accordance with other techniques known to those of ordinary skill in the relevant art or that may be developed in the future. Numerous other embodiments, and modifications thereof, are contemplated as falling within the scope of the present invention as defined by appended claims and equivalents thereto.

What is claimed is:

1. A method of determining and presenting at least one absolute or relative gene expression level from at least one sample, which comprises:
   providing at least one sample, wherein the sample comprises at least one nucleic acid target sequence;
   hybridizing the at least one sample to a nucleic acid probe array, such that the at least one target sequence hybridizes to the probe array;
   measuring emission intensity values from the probe array;
   providing a computer with a computer program, wherein said program is designed to receive one or more sets of emission intensity data corresponding to probes of the probe array;
   determining, with the computer program, at least one absolute or relative gene expression level based, at least in part, on a statistical measure of the emission intensity data, at least one user-selectable statistical parameter, and a p-value calculation; and
   displaying the at least one absolute or relative gene expression level based, at least in part, on at least one user-selectable display parameter, thereby determining and presenting the at least one absolute or relative gene expression level.

2. The method of claim 1, wherein the probe array is a synthesized or spotted probe array.

3. The method of claim 1, wherein the at least one absolute gene expression level is presented to the user as present, absent, or no call.

4. The method of claim 1,
   wherein the at least one relative gene expression level is presented to the user as increase, decrease, or no change.

5. The method of claim 1, wherein for the determination of the at least one absolute gene expression level, a p-value near a first extreme value indicates a high likelihood of the presence of expression and a p-value near a second extreme value indicates a high likelihood of the absence of expression.

6. The method of claim 1, wherein for the determination of the at least one relative gene expression level, a p-value near a first extreme value indicates a high likelihood of increased expression, a p-value near a second extreme value indicates a high likelihood of decreased expression, and a p-value near a point halfway between the first and second extreme values indicates a weak likelihood for an increase or decrease in expression.

7. The method of claim 6, wherein the at least one user-selectable statistical parameter is a p-value threshold value.

8. A computer program product for determining and presenting at least one absolute or relative gene expression level from at least one sample, comprising:
   a computer program, wherein the program comprises:
   an input manager constructed and arranged to receive one or more sets of emission intensity data corresponding to probes of a nucleic acid probe array;
   a statistical analysis determiner constructed and arranged to determine at least one absolute or relative gene expression level based, at least in part, on a statistical measure of the emission intensity data, at least one user-selectable statistical parameter, and a p-value calculation; and an output manager constructed and arranged to display the at least one absolute or relative gene expression level based, at least in part, on at least one user-selectable display parameter.

9. The method of claim 1, wherein the at least one user-selectable statistical parameter is provided to the computer program as part of a data file.

10. The method of claim 1, wherein the at least one user-selectable statistical parameter is a p-value boundary value.

11. The method of claim 1, wherein the at least one user-selectable statistical parameter is an algorithm.

12. The method of claim 1, wherein the at least one user-selectable display parameter is selected from the group consisting of: filtering, sorting, and deleting.

13. The method of claim 1, wherein the display of the at least one absolute or relative gene expression level occurs in part through a graphical plot.

14. The method of claim 11, wherein the algorithm is based on the One-Sided Wilcoxon Signed Rank Test.

15. The method of claim 8, wherein for the determination of the at least one absolute gene expression level, a p-value near a first extreme value indicates a high likelihood of the presence of expression and a p-value near a second extreme value indicates a high likelihood of the absence of expression.

16. The method of claim 8, wherein for the determination of the at least one relative gene expression level, a p-value near a first extreme value indicates a high likelihood of increased expression, a p-value near a second extreme value indicates a high likelihood of decreased expression, and a p-value near a point halfway between the first and second extreme values indicates a weak likelihood for an increase or decrease in expression.

17. The method of claim 8, wherein the at least one user-selectable statistical parameter is a p-value threshold value.

18. The method of claim 8, wherein the at least one user-selectable statistical parameter is a p-value boundary value.

19. A method of determining and presenting at least one absolute or relative gene expression level from at least one sample, which comprises:
   providing at least one sample, wherein the sample comprises at least one nucleic acid target sequence;
   hybridizing the at least one sample to a nucleic acid probe array, such that the at least one target sequence hybridizes to the probe array;
   measuring emission intensity values from the probe array;
   providing a computer with a computer program, wherein said program is designed to receive one or more sets of emission intensity data corresponding to probes of the probe array;
   determining, with the computer program, at least one absolute or relative gene expression level based, at least in part, on a statistical measure of the emission intensity data and at least one user-selectable statistical parameter, wherein the at least one user-selectable statistical parameter is provided to the computer program as part of a data file; and
   displaying the at least one absolute or relative gene expression level based, at least in part, on at least one user-selectable display parameter, thereby determining and presenting the least one absolute or relative gene expression level.

20. The method of claim 19, wherein the at least one user-selectable statistical parameter provided to the computer program is an algorithm, wherein the algorithm analyzes emission intensity values.

* * * * *